United States Patent [19]

Jungheim et al.

[11] Patent Number: 4,902,707
[45] Date of Patent: * Feb. 20, 1990

[54] BICYCLIC PYRAZOLIDINONES, COMPOSITIONS AND USE

[75] Inventors: Louis N. Jungheim; Sandra K. Sigmund, both of Indianapolis, Ind.

[73] Assignee: Eli Lilly and Company, Indianapolis, Ind.

[*] Notice: The portion of the term of this patent subsequent to May 2, 2006 has been disclaimed.

[21] Appl. No.: 729,009

[22] Filed: Apr. 30, 1985

[51] Int. Cl.$^4$ .................. A01N 43/56; A61K 31/415; C07D 231/00
[52] U.S. Cl. ..................................... 514/405; 514/62; 514/63; 514/305; 514/397; 536/55.2; 546/14; 546/135; 548/110; 548/344; 548/359
[58] Field of Search ................... 548/359, 110, 344; 514/405, 62, 63, 305, 397; 536/55.2; 546/135, 14

[56] References Cited

U.S. PATENT DOCUMENTS

| | | | |
|---|---|---|---|
| 4,128,425 | 12/1978 | Greenwald | 96/66 |
| 4,428,960 | 1/1984 | Heck | 548/515 |
| 4,512,924 | 4/1985 | Attwood et al. | 544/61 |

FOREIGN PATENT DOCUMENTS

| | | |
|---|---|---|
| 3317290 | 11/1983 | Fed. Rep. of Germany |
| 143617 | 9/1980 | German Democratic Rep. ..................... 548/359 |
| 2128984 | 5/1985 | United Kingdom |

OTHER PUBLICATIONS

M. A. Breger, *Antibiotiki*, 16, pp. 26–27, (1961) (plus English Translation).
N. K. Kochetkov et al., *J. General Chemistry—U.S.S.R.* (English Translation), vol. 31, pp. 3072–3076, (1961).
J. E. Baldwin et al., *J. Chem. Soc., Chem. Comm.*, pp. 250–252, (1983).
J. E. Baldwin et al., *Tetrahedron*, 40, pp. 4513 to 4525, (1984).
J. E. Baldwin et al., *J. Chem. Soc., Chem. Comm.*, 194–196, (1985).
E. M. Gordon et al., *Tet. Letters*, 24, pp. 3419–3422, (1983).
D. B. Boyd, T. K. Elzey et al., *Tet. Letters*, 27, pp. 3453–3456, (1986).
D. B. Boyd, B. J. Foster et al., *Tet. Letters*, 27, pp. 3457–3460, (1986).
H. Dorn and A. Otto, *Chem. Ber.*, 101, pp. 3287–3301, (1968).
H. Dorn and A. Otto, *Angew. Chem. Int. Ed. Engl.*, 7, pp. 214–215, (1968).
H. Dorn and A. Otto, *Tetrahedron*, 24, pp. 6809–6811, (1968).

*Primary Examiner*—Robert W. Ramsher
*Attorney, Agent, or Firm*—William B. Scanlon; Paul C. Steinhardt; Leroy Whitaker

[57] ABSTRACT

Bicyclic pyrazolidinones which have antimicrobial and/or herbicidal properties are discussed. The use of these compounds in pharmaceutical compositions, herbicidal compositions, and methods for treating bacterial infections and controlling undesired plants is set forth.

19 Claims, No Drawings

BICYCLIC PYRAZOLIDINONES, COMPOSITIONS AND USE

SUMMARY OF THE INVENTION

The invention is directed to antibiotic and/or herbicidal compounds of the formula

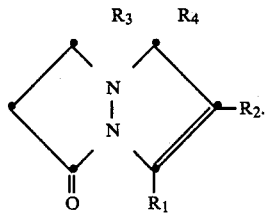

In the above formula, $R_1$, $R_2$, $R_3$ and $R_4$ have the meaning defined for them below.

Further aspects of the invention are pharmaceutical compositions and methods of treatment of gram-positive and gram-negative bacterial infections comprising the use of the above compounds.

DETAILED DESCRIPTION OF THE INVENTION

I. THE INVENTION IN GENERAL; DEFINITION OF TERMS

The present invention embraces compounds of the formula I:

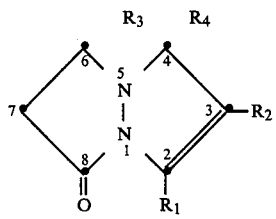

The ring system of the compound in Formula I is a 1,5-diazabicyclo[3.3.0]octa-2-ene ring, often referred to in this Specification as an "unsaturated bicyclic pyrazolidinone" or, more simply, a "bicyclic pyrazolidinone". The numbering system for the ring system is denoted in Formula I.

In the above Formula, the undulating lines connecting $R_3$ and $R_4$ to position 4 of the ring system indicate that the stereochemistry at position 4 could be independently in the R or S configuration. Furthermore, the Formula represents compounds of the invention in various percentage mixtures of the possible enantiomeric and diastereomeric mixtures.

In the above Formula I: either $R_1$ and $R_2$ is hydrogen, $C_1$ to $C_6$ alkyl, $C_1$ to $C_6$ substituted alkyl, perfluoro $C_2$ to $C_4$ alkyl, $C_7$ to $C_{12}$ phenylalkyl, $C_7$ to $C_{12}$ substituted phenylalkyl, phenyl, substituted phenyl, nitro or cyano; a group of the formula $$-CX_3$$

wherein X is fluoro, chloro, bromo or iodo; a group of the formula

wherein Z is 0, 1 or 2 and $R_5$ is $C_1$ to $C_6$ alkyl, $C_1$ to $C_6$ substituted alkyl, phenyl, substituted phenyl, $C_7$ to $C_{12}$ phenylalkyl, $C_7$ to $C_{12}$ substituted phenylalkyl or a heterocyclic ring; a group of the formula $$-COR_6$$

wherein $R_6$ is hydrogen, $C_1$ to $C_6$ alkyl, $C_1$ to $C_6$ substituted alkyl, perfluoro $C_2$ to $C_4$ alkyl, trihalomethyl, $C_7$ to $C_{12}$ phenylalkyl, $C_7$ to $C_{12}$ substituted phenylalkyl, phenyl or substituted phenyl; a group of the formula $$-COOR_7$$

wherein $R_7$ is hydrogen, an organic or inorganic cation, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl, a carboxy protecting group or a non-toxic, metabolically-liable ester-forming group; a group of the formula $$-PO_3(R_8)_2$$

wherein $R_8$ is hydrogen, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, or substituted phenyl; a group of the formula $$-CH_2-N\oplus\equiv Q$$

wherein $-N\oplus\equiv Q$ is a quaternary ammonium group; or a group of the formula $$-CH_2-S-\text{Heterocyclic ring;}$$

and the other of $R_1$ or $R_2$ is a group of the formula $$-COOR_9$$

wherein $R_9$ is hydrogen, an organic or inorganic cation, a carboxy protecting group or a non-toxic, metabolically-labile ester-forming group; and $R_3$ and $R_4$ are the same or different and are hydrogen, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl or a group of the formula $$-COOR_{10}$$

wherein $R_{10}$ has the same definition as $R_7$; with the exception that, when $R_1$ and $R_2$ are a group of the formula $$-COOCH_3,$$

$R_3$ and $R_4$ are not methyl; or a pharmaceutically-acceptable salt thereof.

The protected amino, protected hydroxy and/or protected carboxy compounds represented by Formula I are intermediates to the compounds of Formula I where such groups are in the unprotected form. The unprotected form of the compounds of Formula I possess useful antimicrobial properties and/or herbicidal properties. Thus, the instant antimicrobial compounds can be used to inhibit the growth of microorganisms pathogenic to man and animals and/or control the growth of harmful vegetation.

Another aspect of the invention specifically utilizes the antimicrobial properties of the compounds of Formula I for treating bacterial infections. One part of this aspect encompasses a pharmaceutical composition for the control of gram-positive and gram-negative bacterial infections. The composition comprises a suitable vehicle and a therapeutically effective amount of the compound of Formula I wherein $R_7$ is hydrogen, an organic or inorganic cation, $C_1$ to $C_6$ alkyl, $C_1$ to $C_6$ substituted alkyl, $C_7$ to $C_{12}$ phenylalkyl, $C_7$ to $C_{12}$ substituted phenylalkyl, phenyl, substituted phenyl or a non-tosic, metabolically-labile ester-forming group; and $R_9$ is hydrogen, an organic or inorganic cation or a non-tosic, metabolically-labile ester-forming group.

The second part of this aspect is a method for treating gram-positive and gram-negative bacterial infections. The method comprises administering to the infected host a therapeutically effective amount of the antimicrobial compound of the above pharmaceutical composition.

In the above Formula I, the term "$C_1$ to $C_6$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_6$ alkyl" group is methyl.

The term "$C_1$ to $C_6$ substituted alkyl" denotes the above $C_1$ to $C_6$ alkyl groups that are substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as hydroxymethyl, protected hydroxymethyl, (e.g., tetrahydropyranyloxymethyl), acetoxymethyl, carbamoyloxymethyl, chloromethyl, bromomethyl and iodomethyl.

The term "$C_1$ to $C_4$ alkoxy" as used herein denotes groups such as methoxy, ethoxy, n-propoxy, isopropoxy, n-butoxy, t-butoxy and like groups. Similarly, the term "$C_1$ to $C_7$ acyloxy" denotes herein groups such as formyloxy, acetoxy, propionyloxy, butyryloxy, pentanoyloxy, hexanoyloxy, heptanoyloxy, and the like.

Examples of the term "perfluoro $C_2$ to $C_4$ alkyl" include perfluoroethyl, perfluoro n-propyl, perfluoro iso-propyl, perfluoro n-butyl, perfluoro sec-butyl and the like.

The term "substituted phenyl" specifies a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or methylsulfonylamino. Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(iso-propoxy)phenyl, 4-(t-butoxy)phenyl, 3-ethoxy-4-methoxyphenyl and the like; 3- or 4-trifluoromethylphenyl, a mono- or dicarboxyphenyl or (protected carboxy) phenyl group such as 4-carboxyphenyl or 2,4-di(protected carboxy)phenyl, a mono- or di(hydroxymethyl)phenyl or (protected hydroxymethyl)phenyl such as 3-(protected hydroxymethyl)phenyl or 3,4-di(hydroxymethyl)phenyl, a mono- or di(aminomethyl)phenyl or (protected aminomethyl)phenyl such as 2-(aminomethyl)phenyl or 2,4-(protected aminomethyl)phenyl, or a mono- or di(methylsulfonylamino)phenyl such as 3-(methylsulfonylamino)phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(methylsulfonylamino)phenyl groups.

The terms "halo" and "halogen" refer to fluoro, chloro, bromo or iodo.

The term "trihalomethyl" denotes trifluoromethyl, trichloromethyl, tribromomethyl or triiodomethyl.

The term "$C_7$ to $C_{12}$ phenylalkyl" denotes a $C_1$ to $C_6$ alkyl group substituted at any position by a phenyl ring. Examples of such a group include phenyl methyl(benzyl), 2-phenylethyl, 3-phenyl-(n-propyl), 4-phenylhexyl, 3-phenyl-(n-amyl), 3-phenyl-(sec-butyl) and the like. A preferred group is the benzyl group.

The term "$C_7$ to $C_{12}$ substituted phenylalkyl" denotes a $C_7$ to $C_{12}$ substituted phenylalkyl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or a methylsulfonylamino group. As before, when either the $C_1$ to $C_6$ alkyl portion or the phenyl portion or both are disubstituted, the substituents can be the same or different.

Examples of the term "$C_7$ to $C_{12}$ substituted phenylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)(n-propyl), 4-chloro-3-aminobenzyl, 6-(4-methoxyphenyl)-3-carboxy(n-hexyl), 5-(4-aminomethyl phenyl)-3-(aminomethyl)(n-pentyl) and the like.

The term "organic or inorganic cation" refers to counter-ions for the carboxylate anion of a carboxylate salt. The counter-ions are chosen from the alkali and alkaline earth metals, such as lithium, sodium, potassium, barium and calcium; ammonium, and organic cations such as dibenzylammonium, benzylammonium, 2-hydroxyethylammonium, bis(2-hydroxyethyl)ammonium, phenylethylbenzylammonium, dibenzylethylenediammonium, and like cations. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amine group is referred to by this term. For example, a cation for a carboxylate anion will exist when $R_2$ or $R_1$ is substituted with a (quaternary ammonium)methyl group. A preferred cation for the carboxylate anion is the sodium cation.

The term "pharmaceutically acceptable salt" encompasses those salts that form with the carboxylate anions and includes the organic and inorganic cations discussed above. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic and like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

Furthermore, the compounds of Formula I encompass the requisite negative counter-ion when either $R_1$ or $R_2$ is a (quaternary ammonium)methyl group. Such a counter-ion may be a carboxylate anion at $R_1$ or $R_2$, an anionic group bound at some other place to the bicyclic pyrazolidinone ring or a separate external counter-ion such as a halo or acyloxy anion.

The terms "carboxy-protecting group" and "protected carboxy" as used in the specification refer to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the bicyclic pyrazolidinone molecule and can be removed at the appropriate point without disrupting the remainder of the molecule. In particular, it is important not to subject the carboxy-protected bicyclic pyrazolidinone molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) A preferred carboxylic acid protecting group is the allyl group. Similar carboxy-protecting groups used in the cephalosporin, penicillin and peptide arts can also be used to protect a carboxy group substituents of the bicyclic pyrazolidinones. Further examples of these groups are found in E. Haslam, "Protective Groups in Organic Chemistry" J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The terms "protected hydroxy" and "hydroxy-protecting group" refer to readily cleavable groups bonded to hydroxyl groups, such as the tetrahydropyranyl, 2-methoxyprop-2-yl, 1-ethoxyeth-1-yl, methoxymethyl, $\beta$-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl)dimethylsilyl and 2,2,2-trichloroethoxycarbonyl groups, and the like.

The species of hydroxy-protecting groups is not critical so long as the derivatized hydroxyl group is stable to the conditions of subsequent reaction(s) and can be removed at the appropriate point without disrupting the remainder of the bicyclic pyrazolidinone molecule.

Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy protecting groups are the trityl group and the tetrahydropyranyl group.

The terms "amino-protecting group" and "protected amino" as used in the specification refer to substituents of the amino group commonly employed to block or protect the amino functionality while carrying out reactions at other functional groups on the compound. Examples of such amino protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcychexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, iso-bornyloxycarbonyl, 1-piperidyloxycarbonyl and the like, the benzoylmethylsulfonyl group, the 2-(nitro)-phenylsulfenyl group, the diphenylphosphine oxide group and like amino-protecting groups. The species of amino-protecting group employed is not critical so long as the derivatized amino group is stable to the condition of subsequent reaction(s) on other positions of the bicyclic pyrazolidinone molecule can be removed at the appropriate point without disrupting the remainder of the molecule. Preferred amino-protecting groups are the allyloxycarbonyl, the t-butoxycarbonyl and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

The term "non-toxic, metabolically-labile ester-forming group" refers to those biologically active ester forms which induce increased blood levels and prolong the efficacy of the corresponding non-esterified forms of the compounds. Such ester groups include the lower alkoxymethyl groups, for example, methoxymethyl, ethoxymethyl, iso-propoxymethyl, and the like; the α-($C_1$ to $C_4$)alkoxyethyl groups, for example methoxyethyl, ethoxyethyl, propoxyethyl, iso-propoxyethyl, and the like; the 2-oxo-1,3-dioxolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, α-acetoxymethyl, and the like; the ethoxycarbonyl-1-methyl group; the α-acyloxy-α-substituted methyl groups, for example α-acetoxyethyl, the 3-phthalidyl or 5,6-dimethylphthalidyl groups, the 1-($C_1$ to $C_4$ alkyloxycarbonyloxy)eth- 1-yl groups such as the 1-(ethoxycarbonyloxy)eth-1-yl group; and the 1-($C_1$ to $C_4$ alkylaminocarbonyloxy)eth-1-yl groups such as the 1-(methylaminocarbonyloxy)eth-1-yl group.

In the above Formula I, when $R_1$ or $R_2$ is a (quaternary ammonium)methyl group of the formula

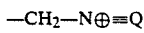

the quaternary ammonium group may be acyclic, cyclic, or a combination of the two, and may contain one or more additional hetero atoms selected from nitrogen, sulfur and oxygen. Examples of acyclic, cyclic and acyclic/cyclic quaternary ammonium groups are found in columns 7, 8, 9, 10 and 36 through 52 of Y. Narita et al., U.S. Pat. No. 4,486,586 ("'586 patent") issued Dec. 4, 1984, herein incorporated by reference. In the incorporated columns 10 and 36 through 52 the quaternary ammonium groups are exemplified as substituents at the 3-position of a prop-1-en-1-yl group, which group is in turn bonded to the 3-position of a cephalosporin ring.

Preferred quaternary ammonium groups are:

(a) a pyridinium ring, which may be substituted once or twice with the following substituents: $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkythio, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ alkylmino, di($C_1$ to $C_4$ alkyl)amino, trifluoromethyl, carboxy, protected carboxy, $C_1$ to $C_4$ alkoxycarbonyl, aminomethyl, protected aminomethyl, carboxymethyl, protected carboxymethyl, carbamoyl, which may be substituted once or twice with a $C_1$ to $C_6$ alkyl group, aminosulfonyl, which may be substituted once or twice with a $C_1$ to $C_6$ alkyl group, sulfonic acid or a substituted or unsubstituted cyclic $C_2$ to $C_{10}$ alkylene or heteroalkylene group;

(b) a quinolinium, isoquinolinium, (1 or 2)-pyradizinium, (1 or 3)-pyrimidinium, (1 or 4)-pyrazinium, thiazolinium, isothiazolinium, oxazolinium, isoxazolinium, (3 or 4)-1,3,4-thiadiazolinium, (2 or 4)-1,2,4-thiadiazolinium, (2 or 5)-1,2,5-thiadiazolinium, (3 or 4)-1,3,4-oxadiazolinium, (2 or 4)-1,2,4-oxadiazolinium, or a (2 or 5)-1,2,5-oxadiazolinium ring, or the mono or di-substituted derivatives thereof, wherein the substituents can be the same or different (and in the case of the quinolinium or isoquinolium rings, on one or both rings) and are amino, protected amino, $C_1$ to $C_4$ alkylamino, di($C_1$ to $C_4$ alkyl)amino, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, cyano, halo, $C_1$ to $C_6$ alkyl, $C_1$ to $C_6$ substituted alkyl, trifluoromethyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, sulfonic acid, carboxy, protected carboxy, $C_1$ to $C_4$ alkoxycarbonyl, hydroxy-($C_1$ to $C_3$ alkyl), protected hydroxy ($C_1$ to $C_3$ alkyl), formyl, $C_2$ to $C_4$ alkanoyl, aminosulfonyl, which may be substituted once or twice with a $C_1$ to $C_6$ alkyl group, carbamoyl, which may be substituted once or twice with a $C_1$ to $C_6$ alkyl group, aminomethyl, protected aminomethyl, carboxymethyl, (protected carboxy)methyl, phenyl, substituted phenyl, benzoyl or benzyl; or (c) a group of the formula

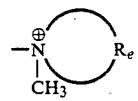

wherein $R_e$ together with the nitrogen atom to which it is attached form a saturated or partially unsaturated 4 to 10 membered heterocyclic ring which may contain one or more further heteroatoms selected from oxygen, nitrogen or sulfur and wherein the substituent may be $C_1$ to $C_6$ alkyl, $C_1$ to $C_6$ substituted alkyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, halo, cyano, hydroxy, protected hydroxy, $C_1$ to $C_4$ alkoxy, $C_1$ to $C_4$ alkylthio, $C_1$ to $C_4$ alkylsulfoxide, $C_1$ to $C_4$ alkylsulfonyl, phenyl, substituted phenyl, formyl, $C_2$ to $C_4$ alkanoyl, benzyl, benzoyl, amino, protected amino, $C_1$ to $C_4$ alkylamino, di($C_1$ to $C_4$ alkyl)amino, trifluoromethyl, carboxy, protected carboxy, $C_1$ to $C_4$ alkoxycarbonyl, aminomethyl, protected aminomethyl, carboxymethyl, protected carboxymethyl, carbamoyl, which may be substituted once or twice with a $C_1$ to $C_6$ alkyl group, aminosulfonyl, which may be substituted once or twice with a $C_1$ to $C_6$ alkyl group, or sulfonic acid, or the benzo-fused analogs of the substituted or unsubstituted, saturated or partially unsaturated ring.

Certain of the terms describing the substituents for the above preferred quaternary ammonium groups have already been defined. Specifically, the terms "$C_1$ to $C_6$ alkyl", "$C_1$ to $C_6$ substituted alkyl", "substituted phenyl", "halo", "$C_1$ to $C_6$ substituted alkyl", "protected carboxy", "protected hydroxy", "protected amino", are as defined above for formula I.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, $C_1$ to $C_6$ alkyl, $C_1$ to $C_4$ alkoxy, carboxy, protected carboxy, amino, or protected amino. The substituent term "$C_5$ to $C_7$ cycloalkenyl" indicates a 1, 2, or 3-cyclopentenyl ring, a 1, 2, 3 or 4-cyclohexenyl ring or a 1, 2, 3, 4 or 5-cycloheptenyl ring, while the term "substituted $C_5$ to $C_7$ cycloalkenyl" denotes the above $C_5$ to $C_7$ cycloalkenyl rings substituted by a $C_1$ to $C_6$ alkyl radical.

The substituent term "$C_1$ to $C_4$ alkylamino" refers to methylamino, ethylamino, n-propylamino, n-butylamino, iso-propylamino and the like. The substituent term "di($C_1$ to $C_4$ alkyl)amino" denotes groups such as dimethylamino, diethylamino, methylethylamino, di(n-butyl)amino, di(n-propyl)amino and the like. Examples of the term "$C_2$ to $C_4$ alkanoyl group" are acetyl, n-propionyl, n-butyryl and the like. The substituent term "$C_1$ to $C_4$ alkoxycarbonyl" refers to groups such as methoxycarbonyl, ethoxycarbonyl, n-propoxycarbonyl, iso-propoxycarbonyl, n-butoxycarbonyl, t-butoxycarbonyl and the like.

The substituent term "$C_1$ to $C_4$ alkylthio" refers to sulfide groups such as methylthio, ethylthio, n-propylthio, iso-propylthio, n-butylthio, t-butylthio and like groups. The substituent term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide, and the like. The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

The term "hydroxy($C_1$ to $C_3$ alkyl)" refers to $C_1$ to $C_3$ alkyl groups substituted at any position by a hydroxy group, such as hydroxymethyl, 2-hydroxyethyl, 1-hydroxyethyl, 3-hydroxy(n-propyl), 2-hydroxy(n-propyl), 1-hydroxy(n-propyl), 1-hydroxy(iso-propyl) and the like. Similarly, the term "protected hydroxy-($C_1$ to $C_3$ alkyl)" refers to $C_1$ to $C_3$ alkyl groups substituted at any position by a protected hydroxy group. Examples of such groups are exemplified when, in the above hydroxy ($C_1$ to $C_3$ alkyl groups), the term "hydroxy" is read as "protected hydroxy".

The substituent term "substituted or unsubstituted cyclic $C_2$ to $C_{10}$ alkylene or heteroalkylene group" defines such a cyclic group bonded ("fused") to the b or c face of the pyridinium ring. The cyclic group may be saturated or contain one or two double bonds. Furthermore, the cyclic group may have one or two alkylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, $C_1$ to $C_4$ alkoxycarbonyl, formyl, $C_2$ to $C_4$ alkanoyl, $C_1$ to $C_6$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the pyridinium radical can contain two to ten ring members, but it preferably contains three to five members. Examples of such saturated cyclic groups are when the pyridinium group is fused to a cyclopentano, cyclohexano or cycloheptano ring. When the cyclic groups are unsaturated, examples occur when the pyridinium ring is fused to a cyclopenteno, cyclohexeno or cycloheptano ring. Examples of fused cyclic groups which each contain one oxygen atom and one or two double bonds are when the pyridinium ring is fused to a furo, pyrano, dihydrofuro or dihydropyrano ring, and examples of cyclic groups which each have one sulfur atom and contain one or two double bonds are when the pyridinium ring is fused to a thieno, thiopyrano, dihydrothieno or dihydrothiopyrano ring. Examples of cyclic groups which contain two heteroatoms selected from sulfur and nitrogen and one or two double bonds are when the pyridinium ring is fused to a thiazolo, isothiazolo, dihydrothiazolo or dihydroisothiazolo ring. Examples of cyclic groups which contain two heteroatoms selected from oxygen and nitrogen and one or two double bonds are when the pyridinium ring is fused to an oxazolo, isoxazolo, dihydrooxazolo or dihydroisoxazolo ring. Examples of cyclic groups which contain two nitrogen heteroatoms and one or two double bonds occur when the pyridinium ring is fused to a pyrazolo, imidazolo, dihydropyrazolo or dihydroimidazolo ring.

The b or the c side of the pyridinium group can be fused to a cyclic group with three ring members. In the case of such a cyclic group containing only one heteroatom, the position of the heteroatom can result in a [2,3], [3,2] or [3,4] fusion with the pyridinium group. When the three-membered cyclic group contains two heteroatoms, the position of the heteroatoms can be such that they result in a [4,5], [5,4], [3,4] or [4,3] fusion with the pyridinium group.

Similarly, the b or c side of the pyridinium group can be fused to a cyclic group with four ring members. Such a cyclic group containing only one heteroatom can result in a [3,2], [2,3], [3,4] or [4,3] fusion with the pyridinium group. The four membered cyclic group with two heteroatoms can result in a [4,5], [5,4], [3,4], [4,3], [5,6] or [6,5] fusion to the pyridinium group.

Examples of the bicyclic pyridinium-containing ring systems that can result when the pyridinium ring is substituted with a $C_2$ to $C_{10}$ alkylene or substituted alkylene group includes groups of the formula:

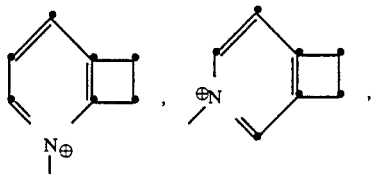

and groups such as: 5H-1-pyrindinium, 7H-1-pyrindinium, 1H-2-pyrindinium, 5H-2-pyrindinium, thieno[3,2-b]pyridinium, thieno[3,2-c]pyridinium, thieno[2,3-c]pyridinium, thieno[2,3-b]pyridinium, thieno[3,4-c]pyridinium, furo[3,2-b]pyridinium, furo3,2-c]pyridinium, furo[3,4-b]-pyridinium, oxazolo[4,5-b]pyridinium, oxazolo[5,4-b]pyridinium, oxazolo[4,5-c]pyridinium, oxazolo[5,4-c]pyridinium, thiazolo[4,5-b]pyridinium, thiazolo[5,4-b]pyridinium, thiazolo[4,5-c]pyridinium, thiazolo[5,4-c]pyridinium, 5,6,7,8-tetrahydroquinolinium, 5,6-dihydroquinolinium, 7,8-dihydroquinolinium, 5,6,7,8-tetrahydroisoquinolinium, 5,6-dihydroisoquinolinium, 7,8-dihydroisoquinolinium, 1,5-naphthyridinium, 1,6-naphthyridinium, 1,7-napthyridinium, 1,8-napthyridinium, 2,6-napthyridinium, 2,7-napthyridinium, 2H-pyrano[3,2-c]pyridinium, 5H-pyrano[4,3-b]pyridinium, 1H-pyrano[3,4-b]pyridinium, 2H-pyrano[2,3-b]pyridinium, 1H-pyrano[4,3-c]pyridinium, 1H-pyrano[3,4-c]pyridinium, 5H-thiopyrano[4,3-b]pyridinium, 4H-thiopyrano[2,3-b]pyridinium, pyrido[3,2-d]pyrimidin-5-yl, pyrido[4,3-d]pyrimidin-6-yl, pyrido[3,4-d]pyrimidin-7-yl, pyrido[2,3-d]pyrimidin-8-yl, pyrido[2,3-b]pyrazin-5-yl, pyrido[3,4-b]pyrazin-6-yl, pyrido[2,3-d]pyridazin-1-yl, pyrido[3,4-d]pyridazin-6-yl, 4H-pyrido[2,3-d][1,3]oxazin-8-yl, 2H-pyrido[4,3-b][1,4]oxazin-6-yl, 5H-pyrido[2,3-d][1,2]oxazin-1-yl, 8H-pyrido[3,2-d][1,2]oxazin-1-yl, 1H-pyrido[2,3-b][1,4]thiazin-5-yl, 3H-pyrido[2,3-b][1,4]thiazin-5-yl, 2H-pyrido[4,3-b][1,4]thiazin-6-yl, 6,7-dihydro-5H-1-pyrindinium, 6,7-dihydro-5H-2-pyrindinium, 2,3-dihydro-furo[3,2-b]pyridinium, 2,3-dihydro-furo[2,3-b]pyridinium, 2,3-dihydro-thieno[2,3-b]pyridinium, 2,3-dihydro-thieno[3,2-b]pyridinium, 2,3-dihydro-thieno[2,3-c]pyridinium, the substituted derivatives thereof, and the like.

A preferred quaternary ammonium group is a substituted or unsubstituted pyridinium ring.

The substituted pyridinium ring can be substituted once or twice with the above-listed substituents. When the ring is substituted twice, the substituents may be the same or different.

Examples of a group of more particularly preferred substituents on the pyridinium ring are: 3-methyl, 4-methyl, 3-ethyl, 2-ethyl, 4-ethyl, 4-propyl, 3-(iso-propyl), 2-methyl, 2-(pent-3-yl), 4-(t-butyl), 2,4-dimethyl, 3,4-dimethyl, 3,5-dimethyl, 2,5-dimethyl, 3-ethyl-4-methyl, 3-methyl-4-ethyl, 3-ethyl-6-methyl, 2-benzyl, 4-benzyl, 4-phenyl, 3-phenyl, 2-(hydroxymethyl), 3-(hydroxymethyl), 4-(hydroxymethyl), 3-hydroxy, 2-(1-hydroxyeth-1-yl), 3-(1-hydroxyeth-1-yl), 4-(1-hydroxyeth-1-yl), 3-(2-hydroxyprop-2-yl), 4-(2-hydroxyprop-2-yl), 3-(3-hydroxyprop-1-yl), 3-acetyl, 4-acetyl, 3-benzoyl, 4-benzoyl, 3-methoxy, 4-methoxy, 4-ethoxy, 3-ethoxy, 4-methoxymethyl, 2-methylthio, 4-methylthiomethyl, 3-fluoro, 4-(N-acetamido), 3-ethoxycarbonyl, 4-ethoxycarbonyl, 3-methoxycarbonyl, 3-ethoxycarbonyl, 3-carbamoyl, 4-(N-ethylcarbamoyl), 3-(N,N-diethylcarbamoyl), 4-cyano, 4-(aminosulfonyl), 4-(potassium eth-1-yl-2-sulfonate), 4-cyclopentyl, 4-(p-chlorobenzyl), 3-alkyl, 5-hydroxy-2-methyl, 3-hydroxy-4-methyl, 4-(1-hydroxypropyl), 3-(1-hydroxypropyl), 3-(2-hydroxy-2-methylpropyl), 2-(hydroxymethyl)-4-methyl, 2-(1,3-dihydroxyprop-2-yl), 4-(2-hydroxypropyl), 4-(3-hydroxypropyl), 3-cyclohexyl, 4-cyclohexyl, 3-cyclopentyl, 4-(cyclohex-1-enyl), 3-(cyclohex-1-enyl), 4-(cyclopent-1-enyl), 3-(cyclopent-1-enyl), 3-(cyclohept-1-enyl), 3-(4-methylcyclohex-1-enyl), 3-(1-hydroxycyclohexyl), 3-(1-hydroxycyclopentyl), 4-(1-hydroxycyclohexyl), 4-(1-hydroxycyclopentyl), 3-(1-hydroxycycloheptyl), 4-methoxy-3-methyl, 3-methoxy-4-methyl, 3-(iso-propoxy), 3-propoxy, 2-(1-methoxyeth2-yl), 4-(2-ethoxyeth-1-yl), 2-(2-ethoxyeth-1-yl), 4-(acetylmethyl), 4-(3-chloropropyl), 3-(3-chloropropyl), 3-trifluoromethyl, 3-bromo-4-methyl, 3-(cyanomethyl), 4-(1-hydroxy-1-(sulfonic acid)methyl), 4-(cyclopent-2-enyl), 4-(cyclopropyl) and the various protected hydroxy analogs thereof; and a pyridinium ring substituted with the above-described $C_2$ to $C_{10}$ alkylene or heteroalkylene ring, resulting in the following bicyclic ring examples: 5,6-dihydro-5H-1-pyrindinium, 5,6,7,8-tetrahydroquinolinium, 5,6,7,8-tetrahydroisoquinolinium, 3-methyl-5,6,7,8-tetrahydroquinolinium, 6,7-dihydro-5H-2-pyrindinium, 7-hydroxy-5,6-dihydro-5H-1-pyrindinium, 5,6,8,9-tetrahydro-7H-cyclohepta[b]pyridinium, 2,3-dihydro-furo[2,3-b]pyridinium, 3-hydroxy-2,3-dihydro-furo[2,3-b]pyridinium, 3-keto-2,3-dihydro-furo[2,3-b]pyridinium, thieno[3,2-b]pyridinium, thieno[3,2-c]pyridinium, furo[3,2-c]pyridinium, 2-methylthiazolo[4,5-c]pyridinium, and 2-methylthiazolo[5,4-c]pyridinium.

A preferred group of substituted pyridinium rings are 4-carbamoylpyridinium, 4-(eth-2-yl-1-sulfonic acid)-pyridinium, 4-(sodium eth-2-yl-1-sulfonate)pyridinium, 5,6-dihydro-5H-1-pyrindinium, thieno[3,2-b]pyrindinium, thieno[3,2-c]pyridinium, furo[3,2-c]pyridinium, 2-methylthieno[4,5-c]pyridinium and 2-methylthieno[5,4-c]pyridinium.

A more preferred group of pyridinium rings is pyridinium, 4-carbamoylpyridinium, 4-(sodium eth-1-yl-2-sulfonate)pyridinium, 5,6-dihydro-5H-1-pyrindinium, 2-methylthiazolo[4,5-c]pyridinium and 2-methylthiazolo[5,4-c]pyridinium.

Another preferred quaternary ammonium group is the substituted or unsubstituted quinolinium group. The quinolinium group may be substituted on the A or B ring or on both rings by the same or different substituents. Some examples and description of substituted quinolinium groups can be found in W. H. W. Lunn, U.S. Pat. No. 4,396,620, issued Aug. 2, 1983, herein incorporated by reference. Columns 3, 4, 13, 14, 15, 16, 17, 18, 19 and 20 of the '620 patent are particularly helpful in this regard.

A preferred group of quinolinium groups are the quinolinium, 5-aminoquinolinium, 3-aminoquinolinium, 2-aminoquinolinium, 7-aminoquinolinium, 5-hydroxyquinolinium, 6-hydroxyquinolinium and 7-hydroxyquinolinium group.

Another preferred quaternary ammonium group is the substituted or unsubstituted isoquinolinium group. The isoquinolinium ring may be substituted on the A or the B ring or on both rings by the same or different substituents.

Examples and description of substituted isoquinolinium groups can be found in W. H. W. Lunn, U.S. Pat. No. 4,396,619, issued Aug. 2, 1983, herein incorporated by reference. Columns 3, 4, 13, 14, 16, 17, 18, 19, 20, 21 and 22 of the '619 patent are particularly helpful in this regard.

A preferred group of isoquinolinium substituents are isoquinolinium, the hydroxy-substituted isoquinolinium groups such as 5-hydroxyisoquinolinium or 4-hydroxyisoquinolinium, or the amino-substituted isoquinolinium groups such as 4-aminoisoquinolinium, 5-aminoisoquinolinium or 6-aminoisoquinolinium.

A more preferred group of isoquinolinium groups are the isoquinolinium, 5-aminoisoquinolinium and 8-hydroxyisoquinolinium groups.

Another preferred quaternary ammonium group is a 1-pyridazinium or 2-pyridazinium group, or a mono- or di-substituted analog thereof, wherein the substituents can be the same or different.

A preferred group of pyridazinium substituents include: pyridazinium (unsubstituted), 3,6-dichloropyridazinium, 3-methylpyridazinium, 3,6-di(-hydroxy)pyridazinium, 3-chloro-6-methoxypyridazinium, 3,5-di(hydroxy)pyridazinium, 4-methylpyridazinium, 3-methoxypyridazinium, 4-methoxypyridazinium, 3,6-dimethylpyridazinium, 3-(methylthio)pyridazinium, 4-(methylthio)pyridazinium, 3-aminopyridazinium, 4-aminopyridazinium, 3-amino-6-methylpyridazinium, 3,6-di(methoxy)pyridazinium, 6-aminopyridazinium, 6-(methylamino)pyridazinium, 6-chloro-3-methoxypyridazinium, 5-methylpyridazinium, and 5-ethylpyridazinium.

A more preferred pyridazinium group is unsubstituted pyridazinium.

Another preferred quaternary ammonium group is a 1-pyrimidinium or 3-pyrimidinium group, or a mono- or di-substituted analog thereof, wherein the substituents can be the same or different.

A preferred group of pyrimidinium substituents is 4,5-diaminopyrimidinium, 4,6-diaminopyrimidinium, the (protected amino)pyrimidinium analogs thereof, 4-phenylpyrimidinium, 4,6-dichloropyrimidinium, 2,4-dichloropyrimidinium, 4,6-di(methyl)pyrimidinium and the unsubstituted pyrimidinium group. A more preferred pyrimidinium group is unsubstituted pyrimidinium.

Another preferred quaternary ammonium group is the 1-pyrazinium or 4-pyrazinium group, or a mono- or di-substituted analog thereof, wherein the substituents can be the same or different.

A preferred group of pyrazinium substituents include 3-methylpyrazinium, 3,5-di(methyl)pyrazinium, 3-aminopyrazinium, 3-protected aminopyrazinium, 3-ethylpyrazinium, 3-(diethylamino)pyrazinium, 3-(ethylamino)pyrazinium, 3,5-diethylpyrazinium, 3-(dimethylamino)pyrazinium, 2,6-dimethylpyrazinium, 2-chloropyrazinium, 3-chloropyrazinium, 2-aminopyrazinium, 2-carboxy-3-aminopyrazinium, 2,6-dichloropyrazinium, 2,3-dimethylpyrazinium, 2,5-dimethylpyrazinium, 2-methylpyrazinium, 2-carbamoylpyrazinium, 2-carboxypyrazinium, 2,3-dicarbamoylpyrazinium, 2,3-dicarboxypyrazinium, 2-methylpyrazinium, 2-ethylpyrazinium, 2-ethyl-3-methylpyrazinium, 2-ethyl-5-methylpyrazinium, 2-ethyl-6-methylpyrazinium, 2,5-diethylyrazinium, 3-(isopropyl)-2-ethoxypyrazinium, 3-(sec-butyl)-2-methoxypyrazinium and 3-(iso-butyl)-2-methoxypyrazinium. A more preferred group of pyrazinium substituents is the unsubstituted pyrazinium and the 2-(dimethylamino)-pyrazinium-1-yl groups.

Another group of preferred quaternary ammonium substituents is the substituted or unsubstituted thiazolinium, isothiazolinium, oxazolinium, isoxazolinium, 1,3,4-thiadiazolinium, 1,2,4-thiadiazolinium, 1,2,5-thiadiazolinium, 1,3,4-oxadiazolinium, 1,2,4-oxadiazolinium or 1,2,5-oxadiazolinium groups, each of which can be substituted once or twice with the same or different substituents. The groups containing two nitrogen atoms in the ring may be quaternized at either ring nitrogen.

A preferred ring system in this group is the substituted or unsubstituted thiazolium group. A preferred thiazolium group is the 4-methyl-5-(1-hydroxyeth-2-yl)-thiazolium ring.

Also, a preferred quaternary ammonium group is a group of quaternary ammonium substituents which have the formula:

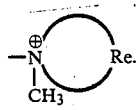

The preferred compounds of the above quaternary ammonium group occur when the variable Re, taken together with the nitrogen atom to which it is attached, represents a saturated or mono-unsaturated 5-, 6-, 7- or 8-membered heterocyclic ring optionally containing a further nitrogen or oxygen heteroatom. The heterocyclic ring may be mono-substituted and may also be fused with a benzene ring.

A preferred substituent within this quaternary ammonium group is of the formula

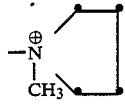

Further examples and description of this type of quaternary ammonium group can be found in P. E. Ayres, U.S. Pat. No. 4,168,309, issued Sept. 18, 1979, herein incorporated by reference.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

A preferred group of examples of the above heterocyclic rings, when $R_1$ or $R_2$ is a heterocyclic thiomethyl group, are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl, triazolyl, preferably 1,3,4-triazol-5-yl, 1,2,3-triazol-5-yl and 1,2,4-triazol-5-yl, and tetrazolyl, preferably 1H-tetrazol-5-yl. A preferred group of examples of benzo-fused derivatives are, in particular, benzoxazol-2-yl, benzthiazol-2-yl, benzimidazol-2-yl and indol-2-yl.

Further specific examples of the above heterocyclic ring systems forming part of a heterocyclic thiomethyl group are 6-membered ring systems containing one to three nitrogen atoms. Such examples include pyridyl, such as pyrid-2-yl, pyrid-3-yl and pyrid-4-yl, pyrimidyl, preferably pyrimid-2-yl and pyrimid-4-yl, triazinyl, preferably 1,3,4-triazin-2-yl and 1,3,5-triazin-4-yl, pyridazinyl, in particular pyridazin-3-yl, and pyrazinyl. The pyridyl, pyrimid-2-yl, pyrimid-4-yl, pyridazinyl and the 1,3,4-triazin-2-yl radicals, the pyridine N-oxides and pyridazine N-oxides, are a preferred group.

The substituents for the optionally substituted heterocyclic ring systems, and further examples of the 5- and 6-membered ring systems discussed above, are found in W. Dürckheimer et al., U.S. Pat. No. 4,278,793, issued July 14, 1981, columns 9 through 21 and columns 33 through 188, herein incorporated by reference. (In columns 33 through 188, the substituents under the heading "A" are examples of "heterocyclic ring" when the ring is a part of heterocyclic thiomethyl group).

A particularly preferred group of examples of the term "heterocyclic ring", when the ring is part of a heterocyclic thiomethyl group, is 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]pyridazin-6-yl.

A most preferred group of examples of the term "heterocyclic ring" when the term is used in conjunction with a heterocyclic thiomethyl group are 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo- 6-hydroxy-2-methyl-as-triazin-3-yl, tetrazolo[1,5-b]pyridazin-6-yl and 8-aminotetrazolo[1,5-b]pyridazin-6-yl.

In the above Formula I, when $R_1$ or $R_2$ is a group of the formula

wherein $R_5$ is a heterocyclic group, examples of such groups are 1,3-thlazol-2-ylthio, 4-(carboxymethyl)-5-methyl-1,3-thiazol-2-ylthio, 4-(carboxymethyl)-5-methyl-1,3-thiazol-2-ylthio sodium salt, 1,2,4-thiadiazol-5-ylthio, 3-methyl-1,2,4-thiadiazol-5-ylthio, 1,3,4-triazol-5-ylthio, 2-methyl-1,3,4-triazol-5-ylthio, 2-hydroxy-1,3,4-triazol-5-ylthio, 2-(carboxy)-4-methyl-1,3,4-triazol-5-ylthio sodium salt, 2-(carboxy)-4-methyl-1,3,4-triazol-5-ylthio, 1,3-oxazol-2-ylthio, 1,3,4-oxadiazol-5-ylthio, 2-methyl-1,3,4-oxadiazol-5-ylthio, 2-(hydroxymethyl)-1,3,4-oxadiazol-5-ylthio, 1,2,4-oxadiazol-5-ylthio, 1,2,4-oxadiazol-5-ylthio, 1,3,4-thiadiazol-5-ylthio, 2-methyl-1,3,4-thiadiazol-5-ylthio, 2thiol-1,3,4-thiadiazol-5-ylthio, 2-(methylthio)-1,3,4-thiadiazol-5-ylthio, 2-amino-1,3,4-thiadiazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(carboxymethyl)-1H-tetrazol-5-ylthio, 1-(carboxymethyl)-1H-tetrazol-5-ylthio sodium salt, 1-(methylsulfonic acid)-1H-tetrazol-5-ylthio, 1-(methylsulfonic acid)-1H-tetrazol-5-ylthio sodium salt, 2-methyl-1H-tetrazol-5-ylthio, 1,2,3-triazol-5-ylthio, 1-methyl-1,2,3-triazol-5-ylthio, 2-methyl- 1,2,3-triazol-5-ylthio, 4-methyl-1,2,3-triazol-5-ylthio, pyrid-2-ylthio N-oxide, 6-methoxy-2-(N-oxide)-pyridaz-3-ylthio, 6-hydroxypyridaz-3-ylthio, 1-methylpyrid-2-ylthio, 1-methylpyrid-4-ylthio, 2-hydroxypyrimid-4-ylthio, 1,4,5,6-tetrahydro-5,6-dioxo-4-methyl-as-triazin-3-ylthio, 1,4,5,6-tetrahydro-4-(2-formylmethyl)-5,6-dioxo-as-triazin-3-ylthio, 2,5-dihydro-5-oxo-6-hydroxy-as-triazin-3-ylthio, 2,5-dihydro-5-oxo-6-hydroxy-as-triazin-3-ylthio sodium salt, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, 2,5-dihydro-5-oxo-6-methoxy-2-methyl-as-triazin-3-ylthio, 2,5-dihydro-5-oxo-as-triazin-3-ylthio, 2,5-dihydro-5-oxo-2- methyl-as-triazin-3-ylthio, 2,5-dihydro-5-oxo-2,6-dimethyl-as-triazin-3-ylthio, tetrazolo[1,5-b]pyridazin-6-ylthio and 8-aminotetrazolo[1,5-b]pyridazin-6-ylthio; the corresponding sulfoxides and sulfones of the above heterocyclic thio groups, and the like.

Examples of the above group when $R_5$ is other than a heterocyclic group include $C_1$ to $C_6$ alkylthio groups such as methylthio, ethylthio, (sec-butyl)thio, (t-amyl)thio and (n-hexyl)thio, $C_7$ to $C_{12}$ alkylphenylthio groups such as 2-phenylpropylthio, benzylthio, 1-phenyl(n-amyl)thio and 4-phenyl(n-butyl)thio; $C_1$ to $C_6$ substituted alkylthio groups such as cyanomethylthio, 2-hydroxyethylthio, 2-nitropropylthio, 2-carbamoyl(sec-butyl)thio, 5-chloroamylthio, 4-carboxyamylthio, 6-carbamoyloxyhexylthio, 2-methoxyethylthio, isopropoxy(t-butyl)thio, 2-aminoethylthio, 2,5-dihydroxyamylthio, 3,3-dibromo(n-butyl)thio, 3-chloro-2-iodopropylthio and 4-acetoxy-6-fluorohexylthio; $C_7$ to $C_{12}$ substituted alkylphenylthio groups such as 3-(3,4-diiodophenyl)propylthio, 1-(3-chloro-4-fluorophenyl)ethylthio, 6-(4-cyanophenyl)hexylthio, 3-phenyl-1-chloro(sec-butyl)thio, 2-phenyl-2-hydroxyethylthio, 5-phenyl-2-hydroxyamylthio, 2-(3-nitrophenyl)-3-ethoxypropylthio, 5,6-dihydroxy-2-(4-ethyl-2-hydroxyphenyl)-hexylthio, and 5-carbamoyl-3-nitro-2-(2,4-dimethoxyphenyl)amylthio; phenylthio, and (substituted phenyl)thio groups, and the corresponding sulfoxide and sulfone analogs thereof.

Examples of the (substituted phenyl)thio groups represented by Rs include groups such as 4-chlorophenylthio, 2,6-dichlorophenylthio, 2,5-dichlorolphenylthio, 3,4-dichlorophenylthio, 3-chlorophenylthio, 3-bromophenylthio, 4-bromophenylthio, 3,4-dibromophenylthio, 3-chloro-4-fluorophenylthio, 2-fluorophenylthio, 4-hydroxyphenylthio, 3-hydroxyphenylthio, 2,4-dihydroxyphenylthio, 3- or 4-nitrophenylthio, 4-cyanophenylthio, 4-methylphenylthio, 2,4-dimethylphenylthio, 2-methylphenylthio, 4-(isopropyl)phenylthio, 4-ethylphenylthio, 3-(n-propyl)phenylthio, 2,6-dimethoxyphenylthio, 4-methoxyphenylthio, 3-ethoxyphenylthio, 4-(iso-propoxy)phenylthio, 4-(t-butoxy)phenylthio, 3-ethoxy-4-methoxyphenylthio, 3- or 4-(trifluoromethyl)phenylthio, 4-carboxyphenylthio, 2,4-di(protected carboxy)phenylthio, 3-(protected hydroxymethyl)phenylthio, 3,4-di(hydroxymethyl)phenylthio, 2-(aminomethyl)phenylthio, 2,4-di(protected aminomethyl)phenylthio, 3-(methylsulfonylamino)phenylthio, 3-methyl-4-hydroxyphenylthio, 3-chloro-4-hydroxyphenylthio, 2-methoxy-4-bromophenylthio, 4-ethyl-2-hydroxyphenylthio, 3-hydroxy-4-nitrophenylthio, 2-hydroxy-4-chlorophenylthio and the corresponding sulfoxide and sulfone analogs thereof.

A preferred group of examples of the group

include: 4-(carboxymethyl)-5-methyl-1,3-thiazol-2-ylthio, 4-(carboxymethyl)-5-methyl-1,3-thiazol-2-ylthio sodium salt, 1,3,4-triazol-5-ylthio, 2-methyl-1,3,4-triazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(carboxymethyl)-1H-tetrazol-5-ylthio, 1-(carboxymethyl)-1H-tetrazol-5-ylthio sodium salt, 1-(methylsulfonic acid)-1H-tetrazol-5-ylthio, 1-(methylsulfonic acid)-1H-tetrazol-5-ylthio sodium salt, 1,2,3-triazol-5-ylthio, 1,4,5,6-tetrahydro-5,6-dioxo-4-methyl-as-triazin-3-ylthio, 1,4,5,6-tetrahydro-4-(formylmethyl)-5,6-dioxo-as-triazin-3-ylthio, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, tetrazolo[1,5-b]pyridazin-6-ylthio, 8-aminotetrazolo[1,5-b]pyridazin-6-ylthio, methylthio, phenylthio, phenylsulfonyl, methylsulfonyl, methylsulfoxide, and phenylsulfoxide.

In the above Formula I, $R_1$ or $R_2$ can be an acyl group of the formula

Examples of such a group include when $R_6$ is: hydrogen (the formyl group); $C_1$ to $C_6$ alkyl, such as acetyl, sec-butylcarbonyl, t-amylcarbonyl and the like; $C_1$ to $C_6$ substituted alkyl, such as (3-cyanopropyl)carbonyl, 4,5-dichloroamylcarbonyl, 2-carboxy-1-nitroethylcarbonyl and the like; phenyl (the benzoyl group); substituted phenyl, for example, 4-methoxybenzoyl, 2,4-dimethylbenzoyl, 3-nitrobenzoyl, 4-trifluoromethylbenzoyl, 2,4-di(alkyloxycarbonyl)benzoyl, 2-(aminomethyl)benzoyl, 3-hydroxy-4-nitrobenzoyl, and the like; $C_7$ to $C_{12}$ phenylalkyl, such as phenylmethylcarbonyl, 2-phenylethylcarbonyl, phenyl(t-butyl)carbonyl, 3-phenylamylcarbonyl and the like; trihalomethyl, such as trifluoroacetyl, trichloroacetyl, tribromoacetyl or triiodoacetyl; $C_7$ to $C_{12}$ substituted phenylalkyl, such as 3-(3,4-diiodophenyl)propylcarbonyl, 1-(3-chloro-4-fluorophenyl)ethylcarbonyl, 6-(4-cyanophenyl)hexylcarbonyl, 3-phenyl-1-chloro(sec-butyl)carbonyl, 2-phenyl-2-hydroxyethylcarbonyl, 5-phenyl-2-hydroxyamylcarbonyl, 2-(3-nitrophenyl)-3-ethoxypropylcarbonyl, 5,6-dihydroxy-2-(4-ethyl-2-hydroxyphenyl)hexylcarbonyl, 5-carbamoyl-3-nitro-2-(2,4-dimethoxyphenyl)amylcarbonyl and the like; or perfluoro $C_2$ to $C_4$ alkyl, such as perfluoropropionyl, perfluorobutyryl, perfluoropentanoyl, and the like.

A preferred group of examples of the acyl group formed with $R_6$ is the acetyl, benzoyl, trifluoroacetyl, trichloroacetyl, tribromoacetyl, and triiodoacetyl groups.

When $R_1$ or $R_2$ in the above Formula I is a carboxyl group of the formula

—COOR$_7$ examples include groups when $R_7$ is: $C_1$ to $C_6$ alkyl, such as ethoxycarbonyl, sec-butoxycarbonyl, t-amyloxycarbonyl and the like; $C_1$ to $C_6$ substituted alkyl, such as (3-cyanopropyloxy)carbonyl, 4,5-dichloroamyloxycarbonyl, 2-carboxy-1-nitroethoxycarbonyl, and the like; phenyl (the phenoxycarbonyl group), substituted phenyl, for example, 4-methoxyphenoxycarbonyl, 2,4-dimethylphenoxycarbonyl, 3-nitrophenoxycarbonyl, 4-trifluoromethylphenoxycarbonyl, 2,4-di(methoxycarbonyl)phenoxycarbonyl, 2-(aminomethyl)phenoxycarbonyl, 3-hydroxy-4-nitrophenoxycarbonyl, and the like; $C_7$ to $C_{12}$ phenylalkyl, such benzyloxycarbonyl, 2-phenylethoxycarbonyl, phenyl(t-butoxy)carbonyl, 3-phenylamyloxycarbonyl and the like; trihalomethyl, such as trifluoromethoxycarbonyl, trichloromethoxycarbonyl, tribromomethoxycarbonyl or triiodomethoxycarbonyl; or $C_7$ to $C_{12}$ substituted phenylalkyl, such as 3-(3,4-diiodophenyl)propoxycarbonyl, 1-(3-chloro-4-fluorophenyl)ethoxycarbonyl, 6-(4-cyanophenyl)hexyloxycarbonyl, 3-phenyl-1-chloro(sec-butoxy)carbonyl, 2-phenyl-2-hydroxyethoxycarbonyl, 5-phenyl-2-hydroxyamyloxycarbonyl, 2-(3-nitrophenyl)-3-ethoxypropoxycarbonyl, 5,6-dihydroxy-2-(4-ethyl-2-hydroxyphenyl)hexyloxycarbonyl, 5-carbamoyl-3-nitro-(2,4-dimethoxyphenyl)amyloxycarbonyl and the like.

Further examples of the above —COOR$_7$; group are when R$_7$ is: an organic or inorganic cation, such ammonium carboxylate, procaine carboxylate, (phenylethylbenzylammonium)carboxylate, phenylglycine carboxylate, lysine carboxylate, lithium carboxylate, potassium carboxylate, sodium carboxylate and the like; a carboxy protecting group, such as allyl carboxylate, p-methoxybenzyl carboxylate, di-(4-methoxy)benzhydryl carboxylate, benzhydryl carboxylate, 2,2,2-trichloroethyl carboxylate, trimethylsilyl carboxylate, (t-butyl)dimethylsilyl carboxylate, β-(trimethylsilyl)ethyl carboxylate, trityl carboxylate, 4,4',4''-trimethoxytrityl carboxylate, p-toluenesulfonylethyl carboxylate, and the like; a nontoxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy)eth-1-yl carboxylate, 1-(methylaminocarbonyloxy)eth-1-yl carboxylate, and the like.

A preferred group of examples of the carboxy group —COOR$_7$ is when R$_7$ is a C$_1$ to C$_6$ alkyl group, a carboxy protecting group, hydrogen or an organic or inorganic cation. An especially preferred group of examples of the above carboxy group is when R$_7$ is methyl, ethyl, hydrogen, allyl, benzyl, or sodium.

Examples of the group —COOR$_{10}$ are given above in conjunction with the carboxy group —COOR$_7$.

A preferred group of examples of the group —COOR$_{10}$ occurs when R$_{10}$ is a C$_1$ to C$_6$ alkyl group. An especially preferred carboxyl group of the above formula is ethyl carboxylate.

In the above Formula I R$_1$ and R$_2$ can be a carboxy group of the formula

—COOR$_9$.

Examples of this group includes groups wherein R$_9$ is: hydrogen (the carboxylic acid); an organic or inorganic cation, such as ammonium carboxylate, procaine carboxylate, phenylethylbenzylammonium carboxylate, phenylglycine carboxylate, lysine carboxylate, lithium carboxylate, potassium carboxylate, sodium carboxylate and the like; a carboxy protecting group, such as allyl carboxylate, 4-methoxybenzyl carboxylate, di-(4-methoxy)benzhydryl carboxylate, benzhydryl carboxylate, 2,2,2-trichloroethyl carboxylate, trimethylsilyl carboxylate, (t-butyl)dimethylsilyl carboxylate, β-(trimethylsilyl)ethyl carboxylate, trityl carboxylate, 4,4',4''-trimethoxytrityl carboxylate, 4-toluenesulfonylethyl carboxylate, and the like; a non-toxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy)eth-1-yl carboxylate, 1-(methylaminocarbonyloxy)eth-1-yl carboxylate and the like.

A preferred group of examples of the carboxyl group —COOR$_9$ occurs when R$_9$ is hydrogen, allyl, benzyl or sodium.

Examples of the phosphonato group

—PO$_3$(R$_8$)$_2$ includes groups wherein R$_8$ is hydrogen (the phosphonic acid moiety), and an organic or inorganic cation, such as disodium phosphonato, dipotassium phosphonato, diammonium phosphonato, and like groups, groups whrein each R$_8$ is a C$_1$ to C$_6$ alkyl group, such as dimethylphosphonato, diethylphosphonato, methylethylphosphonato, methyl(iso-propyl)phosphonato, amylhexylphosphonato, dihexylphosphonato and the like; groups wherein each R$_8$ is a C$_1$ to C$_6$ substituted alkyl group, such as di(2-nitroethyl)phosphonato, (4-chlorobutyl)(2-carboxyethyl)phosphonato, (3-aminoamyl)(aminomethyl)phosphonato, (2-hydroxyethyl)(2-carbamoylethyl)phosphonato, (3-carbamoyloxypropyl)(2-carbamoyloxypropyl)phosphonato, (3-chlorobutyl)(2-bromobutyl)phosphonato and like groups; groups when R$_8$ is phenyl, (the diphenylphosphonato group); groups wherein each R$_8$ group is substituted phenyl, for example, di(4-methoxyphenyl)phosphonato, (4-methoxyphenyl)(2-methoxyphenyl)phosphonato, (3-cyanophenyl)(3-nitrophenyl)phosphonato, (3-chlorophenyl)(2,4-dimethylphenyl)phosphonato, (3-aminophenyl)(2,4-diaminophenyl)phosphonato, di(2,4-dimethoxyphenyl)phosphonato, (2,4-methylphenyl)(2,4-methoxyphenyl)phosphonato, (3,5-dinitrophenyl)(2,4-aminophenyl)phosphonato and the like; groups wherein each R$_8$ is a C$_7$ to C$_{12}$ phenylalkyl radical, such as di(benzyl)phosphonato, di(2-phenylethyl)phosphonato, benzyl(2-phenylethyl)phosphonato, 3-phenylhexyl(phenyl t-butyl)phosphonato and the like; groups wherein each R$_8$ is a C$_7$ to C$_{12}$ substituted phenylalkyl radical, such as di(4-methoxyphenylmethyl)phosphonato, di(3-phenyl-2-hydroxypropyl)phosphonato, di(3-(4-methylphenyl)-4-aminobutyl)phosphonato, (5-(4-cyanophenyl)amyl)(2-phenyl-2-carbamoylethyl)phosphonato, (2-(3,5-dinitrophenyl)ethyl)(2-(4-hydroxyphenyl)ethyl)phosphonato, (4-phenyl-3-aminobutyl)(4-phenyl-2-iodobutyl)phosphonato and like groups.

Furthermore, each of the R$_8$ variables of the above phosphonato group can be chosen from different groups of substituents. For example, one R$_8$ group can be a C$_1$ to C$_6$ alkyl group while the other R$_8$ group is hydrogen, an organic or inorganic cation, C$_1$ to C$_6$ substituted alkyl, phenyl, substituted phenyl, C$_7$ to C$_{12}$ phenylalkyl or a C$_7$ to C$_{12}$ substituted alkylaryl group. Similarly, when one R$_8$ is a C$_1$ to C$_6$ substituted alkyl substituent group, the other R$_8$ can be hydrogen, an organic or inorganic cation, C$_1$ to C$_6$ alkyl, phenyl, substituted phenyl, C$_7$ to C$_{12}$ phenylalkyl or a C$_7$ to C$_{12}$ substituted phenylalkyl group.

A preferred group of phosphonato groups are the phosphonic acid, disodium phosphonato, dipotassium phosphonato, dimethylphosphonato, monomethylphosphonato, diethylphosphonato and diphenylphosphonato groups.

A preferred group of compounds of Formula I occur when:

either R$_1$ or R$_2$ is hydrogen, phenyl, a group of the formula

—CX$_3$, a group of the formula a group of the formula

a group of the formula
ti —COR$_6$, a group of the formula

—COOR$_7$, or a group of the formula

—PO$_3$(R$_8$)$_2$;

the other of R$_1$ or R$_2$ is a group of the formula

—COOR$_9$; and

R$_3$ and R$_4$ are the same or different and are hydrogen, C$_1$ to C$_6$ alkyl, phenyl, substituted phenyl or a group of the formula

—COOR$_{10}$.

A further preferred group of compounds within the above preferred group occurs when:
either R$_1$ and R$_2$ is hydrogen, phenyl, a group of the formula

—CX$_3$, or a group of the formula

—COOR$_7$;

the other of R$_1$ or R$_2$ is a group of the formula

—COOR$_9$;

and R$_3$ and R$_4$ are:
A. the same and are hydrogen, C$_1$ to C$_6$ alkyl, phenyl or a group of the formula —COOR$_{10}$; or B. different, and either R$_3$ and R$_4$ is hydrogen while the other is substituted phenyl.

One highly preferred group of compounds contained within the above further preferred group occurs when either R$_1$ and R$_2$ is a group of the formula

—COOR$_7$ wherein both R$_7$ and R$_9$ are sodium, hydrogen or allyl.
Examples of this group of highly preferred compounds include:
2,3-di(allyl carboxylate)-8-oxo-1,5-diazabicyclo[3.3.0]octa-2-ene,
2,3-di(sodium carboxylate)-8-oxo-1,5-diazabicyclo[3.3.0]octa-2-ene,
2,3-di(allyl carboxylate)-4,4-dimethyl-8-oxo-1,5-diazabicyclo[3.3.0]octa-2-ene,
2,3-di(sodium carboxylate)-4,4-dimethyl-8-oxo-1,5-diazabicyclo[3.3.0]octa-2-ene,
2,3-di(allyl carboxylate)-4,4-diphenyl-8-oxo-1,5-diazabicyclo[3.3.0]octa-2-ene,
2,3-di(sodium carboxylate)-4,4-diphenyl-1,5-diazabicyclo[3.3.0]octa-2-ene,
2,3-di(allyl carboxylate)-4,4-di(ethyl carboxylate)-8-oxo-1,5-diazabicyclo[3.3.0]octa-2-ene,
2,3-di(sodium carboxylate)-4,4-di(ethyl carboxylate)-8-oxo-1,5-diazabicyclo[3.3.0]octa-2-ene monohydrate,
2,3-di(allyl carboxylate)-4-(R,S)-(2-(trifluoromethyl)phenyl)-8-oxo-1,5-diazabicyclo[3.3.0]octa-2-ene,
2,3-di(sodium carboxylate)-4-(R,S)-(2-(trifluoromethyl)phenyl)-8-oxo-1,5-diazabicyclo[3.3.0]octa-2-ene,
2,3-di(allyl carboxylate)-4-(R,S)-(3-(trifluoromethyl)phenyl)-8-oxo-1,5-diazabicyclo[3.3.0]octa-2-ene and
2,3-di(sodium carboxylate)-4-(R,S)-(2-(trifluoromethyl)phenyl)-8-oxo-1,5-diabicyclo[3.3.0]octa-2-ene.

Another highly preferred group of compounds contained within the above further preferred group occurs wherein R$_1$ is hydrogen, phenyl or a group of the formula —COOCH$_3$, and R$_2$ is a group of the formula

—COOR$_9$ wherein R$_9$ is hydrogen, sodium cation or allyl. Examples of these highly preferred compounds include:
2-phenyl-3-(allyl carboxylate)-8-oxo-1,5-diazabicyclo[3.3.0]octa-2-ene,
2-phenyl-3-(sodium carboxylate)-8-oxo-1,5-diazabicyclo[3.3.0]octa-2-ene,
2-phenyl-3-(allyl carboxylate)-4,4-dimethyl-8-oxo-1,5-diazabicyclo[3.3.0]octa-2-ene,
2-phenyl-3-(sodium carboxylate)-4,4-dimethyl-8-oxo-1,5-diazabicyclo[3.3.0octa-2-ene,
3-(allyl carboxylate)-4,4-dimethyl-8-oxo-1,5-diazabicyclo[3.3.0]octa-2-ene,
3-(sodium carboxylate)-4,4-dimethyl-8-oxo-1,5-diazabicyclo[3.3.0]octa-2-ene,
2-(methyl carboxylate)-3-(allyl carboxylate)-8-oxo-1,5-diazabicyclo[3.3.0]octa-2-ene, and
2-(methyl carboxylate)-3-(sodium carboxylate)-8-oxo-1,5-diazabicyclo[3.3.0]octa-2-ene.

Another highly preferred class of compounds contained within the above group of further preferred compounds occurs wherein R$_1$ is a group of the formula

—COOR$_9$ wherein R$_9$ is hydrogen, sodium or alkyl, R$_2$ is a group of the formula

—COOCH$_3$ and R$_3$ and R$_4$ are the same and are hydrogen. Examples of these compounds include:
2-(allyl carboxylate)-3-(methyl carboxylate)-8-oxo-1,5-diazabicyclo[3.3.0]octa-2-ene and
2-(sodium carboxylate)-3-(methyl carboxylate)-8-oxo-1,5-diazabicyclo[3.3.0]octa-2-ene.

Yet another group of highly preferred compounds contained within the above group of further preferred group occurs when R$_1$ is a group of the formula

—COOR$_9$ wherein R$_9$ is benzyl, allyl, sodium or hydrogen, R$_2$ is a group of the formula

—CF₃ and R₃ and R₄ are each hydrogen. An example of such a highly preferred compound is 2-(benzyl carboxylate)-3-(trifluoromethyl)-8-oxo-1,5-diazabicyclo[3.3.0]octa-2-ene.

Further definitions of terms used in the claims, especially those claims concerning pharmaceutical compositions and methods and herbicidal compositions and methods, are found in succeeding parts of the application.

II. Synthesis of the Compounds of Formula I and the Requisite Starting Materials The bicyclic pyrazolidinones of Formula I are prepared by two methods of a 1,3-dipolar cycloaddition reaction. In the first method, a substituted acetylene moiety is reacted with a 1,3-dipole ("ylide") to give the 2,3-unsaturated bicyclic pyrazolidinone ring system. The second method involves the reaction of a substituted ethylene moiety with an ylide to give the 2,3-saturated pyrazolidinone ring system. The 2,3-saturated system is then reacted with a non-nucleophilic base to give the 2,3-unsaturated system.

The first type of cycloaddition reaction, (i.e., reaction of an ylide with a substituted acetylene) is represented below by Scheme 1:

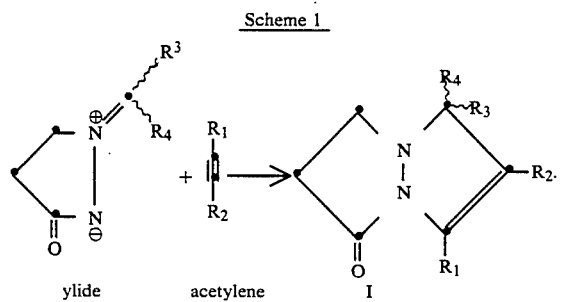

In the above Scheme 1, for brevity's sake, Formula I indicates only one of the two possible 2,3-regioisomer products of the reaction. The reaction represented by Scheme 1 can also produce the opposite 2,3-regioisomer, as well as a mixture of the regioisomers.

In the above Scheme $R_1$, $R_2$, $R_3$ and $R_4$ are as defined above for Formula I. When carrying out the reaction it is preferable to derivatize with protecting groups any of the acidic groups represented by $R_1$, $R_2$, $R_3$ or $R_4$. Examples of such acidic groups are the carboxylic acid group and the hydroxyimino group. It is especially preferred that any carboxylic acid groups be protected.

The reaction should be carried out in aprotic solvents. Examples of such solvents are the chlorinated hydrocarbons, the aromatic hydrocarbons and alkyl or aromatic cyano solvents. The preferred solvents for the above reaction are dichloromethane, acetonitrile, and 1,2-dichloroethane.

The temperature for the reaction is not critical. It is preferred that the reaction be carried out between about room temperature to about the reflux temperature of the solvent. When $R_3$ and $R_4$ are hydrogen, a more preferred temperature is the reflux temperature of the solvent. For any other combination of $R_3$ and $R_4$, a more preferred temperature is approximately room temperature.

The reaction usually requires a period of about 1 to about 168 hours. The optimal reaction time can be determined by monitoring the progress of the reaction by conventional means such as chromatographic techniques (thin layer chromatography, high performance liquid chromatography, or column chromatography) or spectroscopic methods (such as infrared spectroscopy, nuclear magnetic resonance spectrometry and mass spectrometry), or a combination of the two methods.

The usual stoichiometry for the reaction is a 1:1 ratio of ylide to acetylene reagent. Of course, an excess of either reagent is permissible. It is preferred that the acetylene reagent be present in excess, and especially preferred that the acetylene be present in a 2:1 excess. Furthermore, the order of addition of either reagent is not critical.

The regiospecificity of the cycloaddition in Scheme 1 is unpredictable. The stereochemical and electronic properties of the ylide and acetylene and the various reaction conditions have as yet yielded no clearly discernable trends in the regiospecificity of the reaction. Usually the reaction yields widely varying mixtures of 2,3-regioisomer products.

The second type of method for the synthesis of bicyclic pyrazolidinone compounds comprises a two step sequence. In the first step, a 1,3-dipole (ylide) is reacted with a 2-(alkyl or aryl sulfonyl)-1-(substituted or unsubstituted)carboxyethylene moiety. In the second step the elements of (alkyl or aryl)sulfinic acid are eliminated from the 2,3-dihydro ("saturated system") bicyclic pyrazolidinone ring system with a non-nucleophilic base to give the corresponding 2,3-unsaturated system. The second method of cycloaddition reaction is represented by Scheme 2:

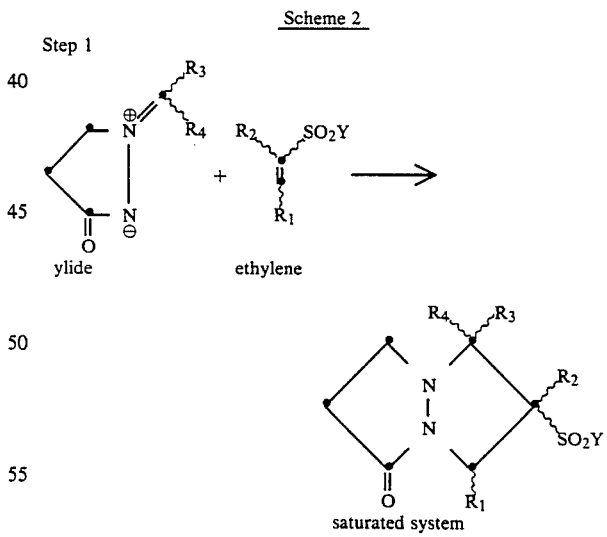

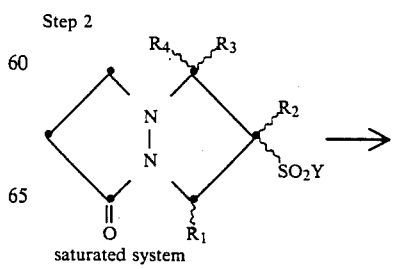

-continued
Scheme 2

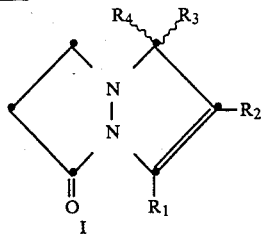

In Scheme 2, $R_3$ and $R_4$ are the same as for Scheme 1. $R_1$ and $R_2$ are the same as for Scheme I except that they are not a phosphonato group or a (quaternary ammonium)methyl group. The symbol "—$SO_2Y$" represents an alkyl- or arylsulfonyl group. When carrying out the reaction of the above Scheme 2, it is preferable to derivatize with protecting groups any acidic groups represented by $R_1$, $R_2$, $R_3$, $R_4$ or Y.

The regiospecificity of the cycloaddition reaction represented by Step 1, Scheme 2 is such that the 3-(alkyl- or arylsulfonyl) regioisomer is the predominant product. Thus, the second cycloaddition reaction method is especially useful for placing the substituent bonded to the sulfonyl-substituted carbon of the ethylene at the 3-position of the bicyclic pyrazolidinone ring. This feature of the reaction makes it an especially useful route to compounds with a substituted methyl group at $R_2$. Examples of such a substituted methyl groups are represented by the formula

—$CH_2X$ wherein X can be halo, hydroxy, protected hydroxy, acyloxy, carbamoyloxy, heterocyclicthio or a group of the formula

S—$R_5$ wherein $R_5$ is other than a heterocyclic ring, as defined above.

A bicyclic pyrazolidinone ring substituted at $R_2$ with halomethyl or acyloxymethyl provides an excellent intermediate for the synthesis of the corresponding (quaternary ammonium)methyl or heterocyclic thio) methyl analogs. The acyloxy or halo substituent on the methyl group of the intermediate is displaced by the amine of the quaternary ammonium group or the thiol of the heterocyclic thio group. The conditions for these displacements are well known and are described in the cephalosporin art for the analogous displacements of halo and acetoxy groups of 3-(halomethyl or acetoxymethyl)cephalosporins.

The solvents, temperature, time, and order of addition for the cycloaddition depicted in Scheme 2 is analogous to the cycloaddition reaction depicted above in Scheme 1. The usual stoichiometry of the reaction is a 1:1 ratio of ylide to ethylene reagent. It is also permissable to use an excess of either reagent.

For the elimination reaction labelled "Step 2" in the above Scheme 2, the preferred solvent is dichloromethane. The elimination is conducted at a temperature from about −78° C. to about room temperature. A non-nucleophilic base, such as 1,8-diazabicyclo[5.4.0]undec-7-ene ("DBU") or 1,5-diazabicyclo[4.3.0]non-5-ene ("DBN"), is used to eliminate the elements of (alkyl or aryl)sulfinic acid. An excess of the non-nucleophilic base in relation to the "saturated system" is normally used.

The reactions and the 2,3-dihydro bicyclic pyrazolidinone compounds of Scheme 2 are further described in L. N. Jungheim and S. K. Sigmund, U.S. Application Ser. No. 728,716, now abandoned filed this even date, currently pending as continuation application Ser. No. 934,054, filed Nov. 24, 1986, now U.S. Pat. No. 4,826,992, herein incorporated by reference. The subject matter of application Ser. No. 728,716, filed this event date, has been carried forward in the continuation application of the same inventors, filed Nov. 24, 1986, application Ser. No. 934,054, herein incorporated by reference.

The antimicrobial activity of the bicyclic pyrazolidinones is further enhanced on removal of any remaining amino, hydroxy and/or carboxy protecting groups on the molecule. As discussed above, such removal methods are well known in the cephalosporin, penicillin and peptide arts. Once the carboxy groups are deprotected, the oral ester group(s) may be put in place on the desired carboxy groups at $R_1$, $R_2$, $R_3$ and $R_4$. The methods for making the oral ester derivatives are well known in the cephalosporin and penicillin art.

The pyrazolidinium ylide starting materials for the cycloaddition reactions in Schemes 1 and 2 are synthesized according to the process depicted below in Scheme 3.

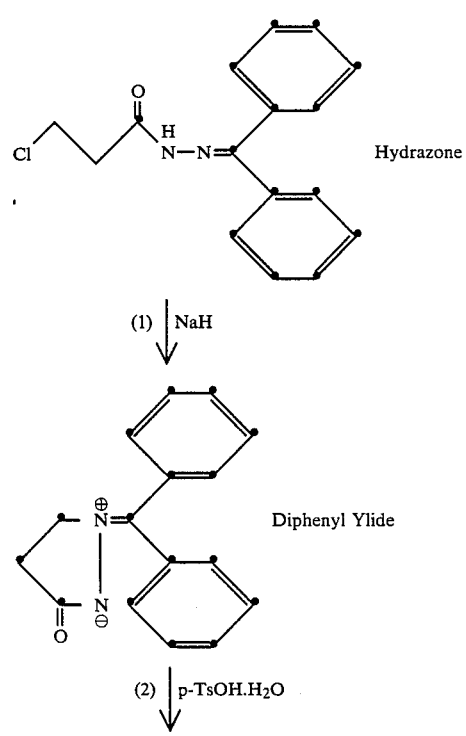

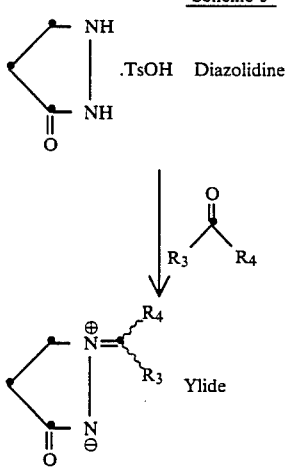

In the above Scheme 3, $R_3$ and $R_4$ are as described above for Formula I.

The first step in the synthesis of the ylide starting materials, represented by Reaction 1 in the above Scheme, is a cyclization of the β-chloropropionylhydrazone of benzophenone ("hydrazone") to the 3-oxo-1-(diphenylmethylene)-1,2-pyrazolidinium ylide ("diphenyl ylide") moiety. The cyclization is carried out using sodium hydride in tetrahydrofuran. The reaction solution is stirred at room temperature for 18 hours then at reflux for 2 hours. The synthesis of the hydrazone and the conditions for Reaction 1 are described in E. C. Taylor et al., *J. Am. Chem. Soc.*, 1981, 103, 7743–7752.

The second step, represented in the above Scheme by Reaction 2, is the hydrolysis of the diphenyl ylide to give the 3-oxo-1,2-diazolidine p-toluene sulfonate salt ("diazolidine") compound. The diphenyl ylide is hydrolyzed with one equivalent of p-toluenesulfonic acid monohydrate in dichloromethane and the hydrolysis is generally complete after 2 hours of stirring at room temperature. The conditions for Reaction 2 are adopted from E.C. Taylor et al., supra.

The final reaction in the synthesis of the pyrazolidinium ylide starting materials, represented as Reaction 3 in the above scheme, is the condensation of a ketone or aldehyde with a diazolidine to give the pyrazolidinium ylide. The diazolidine and the ketone or aldehyde are combined either in equimolar amounts or with an excess of the ketone or aldehyde in a solvent chosen from methanol, ethanol or dimethylformamide. Within a minute or two after combining the two reagents in the solvent, excess solid sodium bicarbonate is added and the resultant solution is stirred for 1 or 2 hours at room temperature. As a useful alternative procedure, the ketal of the ketone may be condensed with the diazolidine in the presence of an acid. For example, the diazolidine reagent is combined with acetone dimethyl acetal in methanol and then the solution is treated with d-10 camphorsulfonic acid. The mixture is refluxed for 1.5 hours to give the dimethyl ylide (i.e., $R_3$ and $R_4$ are methyl). When $R_3$ and $R_4$ are different, those skilled in the art will recognize that this final reaction will produce a mixture of E and Z isomers. The pyrazolidinium ylide products of this reaction can often be employed without further purification.

The acetylene and ethylene starting materials in Schemes I and II, respectively, are made by methods known in the art. The synthesis of some acetylene and ethylene starting materials are also described in the Experimental Section below.

Procedures for the reactions in the above Scheme 3 are found at Preparations 1 through 7 in the Experimental Section.

III. Description of the Antimicrobial Properties of the Bicyclic Pyrazolidinones The compounds of Formula I inhibit the growth of certain pathogenic organisms as demonstrated by standard agar-plate disc-diffusion tests. Table I summarizes the results of such tests with the representative compounds listed below. Antimicrobial activity is measured by the size (diameter in mm) of the observed zone in which growth of the microorganism is inhibited by the test compound.

TABLE 1

Zone of Bacterial and Fungal Growth Inhibition[1]
By Agar-Plate Disc-Diffusion Test

| Organism | Test Compound[2] | | | | | | | | | |
|---|---|---|---|---|---|---|---|---|---|---|
| | 1 | 2 | 3 | 4 | 5 | 6 | 7 | 8 | 9 | 10 |
| *Staphylococcus aureus* X1 | 15 | —[4] | 16 | — | 10 | tr | 12 | tr | — | — |
| *Bacillus subtilis* X12 | 14 | — | 13 | tr | 10 | tr | 15 | tr | — | tr |
| *Bacillus subtilis* X12M[3] | 23 | 10 | 18 | 11 | 22 | 14 | 19 | 15 | — | 12 |
| *Sarcina lutea* X186 | 19 | tr[5] | 25 | 11 | 22 | 10 | 12 | 11 | — | tr |
| *Bacillus stearothermophilus* C451 | 20 | — | 27 | tr | 28 | tr | 14 | 14 | — | tr |
| *Mycobacterium avium* X85 | 15 | — | 30 | 10 | 25 | — | — | 15 | — | tr |
| *Escherichia coli* X161 | — | — | tr | — | — | — | tr | — | — | — |
| *Escherichia coli* X161M[3] | 15 | — | 12 | — | 13 | — | — | tr | — | — |
| *Pseudomonas solanacearum* X185 | — | — | 11 | — | tr | — | — | — | — | — |
| *Escherichia coli* X580 | 21 | — | 30 | tr | 23 | — | 18 | 13 | — | tr |
| *Saccharomyces pastorianus* X52 | — | — | tr | — | — | — | tr | — | — | — |
| *Neurospora crassa* 846 | 14 | — | 10 | — | — | — | 13 | — | — | — |
| *Trichophyton mentagrophytes* A23 | 11 | — | — | — | — | — | 23 | — | — | — |

TABLE 1-continued

Zone of Bacterial and Fungal Growth Inhibition[1]
By Agar-Plate Disc-Diffusion Test

| Organism | Test Compound[2] | | | | | | | | | |
|---|---|---|---|---|---|---|---|---|---|---|
| | 1 | 2 | 3 | 4 | 5 | 6 | 7 | 8 | 9 | 10 |
| *Candida albicans* A26 | tr | — | — | — | — | — | tr | — | — | — |

*Numerals and letters following the names of test microorganisms refer to the strains.
[1]The test compounds were dissolved in water at a concentration of 10 mg/ml; a 7 mm disc was dipped into the suspension and then placed on the agar surface; cultures were incubated 24–48 hours at 25–35° C.
[2]Test compounds numbered 1–10 are as follows:
1 = 2,3-di(sodium carboxylate)-4,4-dimethyl-8-oxo-1,5-diazabicylo[3.3.0]octa-2-ene
2 = 3-(Sodium carboxylate)-4,4-dimethyl-8-oxo-1,5-diazabicyclo[3.3.0]octa-2-ene
3 = 2-Phenyl-3-(sodium carboxylate)-8-oxo-1,5-diazabicyclo[3.3.0]octa-2-ene
4 = 2-Phenyl-3-(sodium carboxylate)-4,4-dimethyl-8-oxo-1,5-diazabicyclo[3.3.0]octa-2-ene,
5 = 2-(Methyl carboxylate)-3-(sodium carboxylate)-8-oxo-1,5-diazabicyclo[3.3.0]octa-2-ene and the corresponding 2,3-regioisomer
6 = 2,3-di(sodium carboxylate)-8-oxo-1,5-diazabicyclo[3.3.0]octa-2-ene
7 = 2-(benzyl carboxylate)-3-(trifluoromethyl)-8-oxo-1,5-diazabicyclo[3.3.0]octa-2-ene
8 = 2,3-di(sodium carboxylate)-4-(meta-trifluoromethylphenyl)-8-oxo-1,5-diazabicyclo[3.3.0]octa-2-ene
9 = 2,3-di(sodium carboxylate)-4-(ortho-trifluoromethylphenyl)-8-oxo-1,5-diazabicyclo[3.3.0]-octa-2-ene
10 = 2,3-di(sodium carboxylate)-4,4-diphenyl-1,5-diazabicyclo[3.3.0]octa-2-ene
[3]Growth on minimal nutrient agar
[4]The symbol "—" indicates no observable zone
[5]The symbol "tr" indicates a trace zone The antimicrobial compounds of this invention are useful for the therapeutic or prophylactic treatment of infections in warm-blooded animals caused by both gram-positive, gram-negative and acid-fast bacteria.

The antimicrobial can be administered orally, parenterally (e.g. intravenously, intramuscularly or subcutaneously) or as a topical ointment or solution in treating bacterial infections of warm-blooded animals.

A further aspect of this invention is the pharmaceutical compositions of the antimicrobial compounds of Formula 1. In particular, these pharmaceutical compositions are useful for the control of gram-positive and gram-negative bacterial infections and comprise a suitable vehicle and a therapeutically effective amount of the antimicrobial compounds of Formula 1.

With regard to compositions for oral administration (e.g. tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as croscarmellose sodium, microcrystalline cellulose, corn starch, sodium starch glycolate, alginic acid and mutable wetting agents such as sodium lauryl sulfate; and lubricants such as magnesium stearate and other metallic stearates, stearic acid, silicone fluid, talc, waxes oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

The pharmaceutical compositions of the present invention may also be in the form of oral liquid preparations, which may be either (a) aqueous or oily suspensions, solutions, emulsions or syrups; or (b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol or ethyl alcohol; and preservatives such as methyl or propyl p-hydroxybenzoates or sorbic acid.

The pharmaceutical composition can also be for intravenous (IV) use. Specifically, a water soluble form of the antimicrobial compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antimicrobial compound (for example, the hydrochloride salt or sodium salt) can be formulated with a "suitable vehicle". Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antibiotic compounds may be administered in the feed or the drinking water of farm animals. Alternatively, the compounds can be formulated as intramammary preparations with "suitable vehicles" such as long- or quick-release bases.

The antimicrobial compounds of Formula I can be used as surface disinfectants. Solutions containing as little as 0.1 percent by weight of the antimicrobial compound are effective for disinfecting purposes. Preferably, such solutions also can contain a detergent or other cleansing agent. The solutions are useful for disinfecting objects such as glassware, dental and surgical instruments, and surfaces such as walls, floors, and tables in areas where maintenance of sterile conditions is important, for example, hospitals, food-preparation areas, and the like.

The antimicrobial compounds of Formula I can also be formulated in unit dosage form in sterile vials, sterile plastic pouches containing a port with a septum, or sterile, hermetically sealed ampoules. The antimicrobial compound (or the corresponding pharmaceutically-acceptable salt) may be a dry powder or in crystalline or lyophylized form. The amount of the antimicrobial compound per unit dosage may vary from about 250 milligrams to about 10 grams.

A "therapeutically effective amount" of the antimicrobial compounds of Formula I is from approximately 3.5 mg to about 50 mg of compound per kilogram of body weight. This amount generally totals from about 1 gram to about 27 grams per day for an adult human.

A further aspect of this invention is a method for treating or controlling infectious diseases caused by gram-positive and gram-negative organisms in warm-blooded animals. This method comprises administering to the animal a therapeutically effective amount of the instant antimicrobial compounds. A typical daily dose for an adult human in this method is from about 1 gram to about 12 grams.

In practicing this method, the antibiotic can be administered in a single daily dose or in multiple doses per day. The treatment regime may require administration over extended periods of time, e.g., for several days or for from two to three weeks. The amount administered per dose or the total amount administered will depend on such factors as the nature and severity of the infection, the age and general health of the patient, the tolerance of both the patient and the microorganism or microorganisms involved in the infection to the antimicrobial compound.

IV. Description of the Herbicidal Properties of the Bicyclic Pyrazolidinones

The compounds of Formula I display useful herbicidal activity against a variety of weed species. It is preferred that the instant herbicidal compounds be used as preemergent herbicides. The compounds may be incorporated into the soil using a conventional disc or harrow prior to planting the seeds of the desired crop species. Alternatively, the compounds may be applied to the soil surface before emergence of the weed species. In this latter procedure the compounds are merely permitted to leach into the soil with the assistance of rainfall, for example.

The herbicidal compounds of Formula I are preferably employed as a herbicidal composition, which comprises a growth-inhibiting amount of the compounds of Formula I and an agriculturally-acceptable carrier. Such compositions may be sprayable formulations (e.g., wettable powders, emulsifiable concentrates, or dry-flowable forms) or dust compositions or solid, granular compositions. The agriculturally-acceptable carriers for such compositions are well known in the art. A growth-inhibiting amount of the compounds will generally be from about 0.5 to about 15.0 pounds of the compound per acre. The compounds are more preferably applied at rates of about 1.0 to about 8.0 pounds per acre (about 0.28 to about 8.96 kg/ha).

The herbicidal activity of representative compounds of the present invention is illustrated by the following greenhouse tests. Specifically, the herbicidal activity was evaluated at various application rates in a multiple species greenhouse test. Several weed and one crop species were utilized to determine the herbicidal activity and selectivity of the test compounds. The compounds were formulated for application by dissolving the compound into a solvent prepared by combining Toximul R and Toximul S (proprietary blends of anionic and nonionic surfactants manufactured by Stepan Chemical Company, Northfield, Ill.) with a 1:1 (v/v) mixture of acetone:ethanol. The solvent/compound solution was diluted with deionized water and applied in a preemergence fashion to the planted containers using an atomizer. The preemergence treatment was made one day after planting.

Following treatment the containers were moved to the greenhouse and watered as necessary. Observations were made 10 to 13 days after treatment using untreated control plants standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. The type of plant injury sustained by the plants was tabulated using the following code letters:

A = abscission of leaves
B = burned
C = chlorosis
D = death
E = epinasty
F = formative effects
G = dark green
I = increased plant growth
L = local necrosis
N = no germination
P = purple pigmentation
R = reduced germination
S = stunting
U = unclassified injury Table II presents preemergence herbicidal test results administered at 8 lbs/acre.

TABLE II

| | Pre-Emergence Herbicidal Activity | | | | | | | | | |
|---|---|---|---|---|---|---|---|---|---|---|
| | Test Plant | | | | | | | | | |
| Compound[1] | Zinnia | Wildoat | Tomato | Barnyard Grass | Mustard | Large Crabgrass | Pigweed | Velvet-leaf | Fox-tail | Morning glory |
| A | 1 | 1 | 4BS | 2BS | 4BS | 1 | 4RS | 5D | 4BS | 4BS |
| B | 3BS | 4BS | 4BS | 2BS | 4BS | 2B | 5D | 5D | 5D | 4BS |

[1]Test compounds denoted as A and B are as follows:
A = 2,3-di(sodium carboxylate)-4-(3-(trifluoromethyl)phenyl)-8-oxo-1,5-diazabicyclo[3.3.0]octa-2-ene
B = 2,3-di(sodium carboxylate)-4-(2-(trifluoromethyl)phenyl)-8-oxo-1,5-diazabicyclo[3.3.0]octa-2-ene The following Examples are provided to further illustrate the invention. It is not intended that the invention be limited in scope by reason of any of the following Preparations or Examples.

In the following Preparations and Examples, the terms nuclear magnetic resonance spectra, mass spectra, infra-red spectra, ultraviolet spectra, elemental analysis and high performance liquid chromatography are abbreviated n.m.r., m.s., i.r., u.v., anal. and HPLC, respectively. In addition, the adsorption maxima listed for the i.r. spectra are only those of interest and not all of the maxima observed.

The abbreviations THF and DMF stand for tetrahydrofuran and dimethylformamide, respectively.

In conjunction with the n.m.r. spectra, the following abbreviations are used: "s" is singlet, "d" is doublet, "dd" is doublet of doublets, "br. s" is broad singlet, "br. d" is a broad doublet, "t" is triplet, "q" is quartet, "m" is multiplet and "dm" is a doublet of multiplets. "J" indicates the coupling constant in Hertz. "DMSO/d$_6$" is dimethyl sulfoxide where all protons have been replaced with deuterium.

The n.m.r. spectra were obtained on a Varian Associates EM-390 90 MHz or T-60 60 MHz instrument, on a Jeol FX-90 Q90 MHz instrument or on a Brüker Corp. 270 MHz instrument. The chemical shifts are expressed in δ values (parts per million downfield from tetramethylsilane). The field desorption mass spectra were taken on a Varian-MAT 731 Spectrometer using carbon dendrite emitters. Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on a Cary 118 instrument. Thin layer chromatography was carried out on E. Merck silica gel plates.

EXPERIMENTAL SECTION

Preparation 1

3-Oxo-1,2-Diazolidine 4-Toluenesulfonate Salt

3-Oxo-1-(diphenylmethylene)-1,2-pyrazolidinium ylide (approximately 5 g, approximately 19 mmol) was dissolved in methylene chloride (100 ml). Para-toluenesulfonic acid monohydrate (19 mmol) was added and the resultant solution was stirred at room temperature for 2 hours. The precipitate that formed was collected by filtration and dried in vacuo over 3 Å molecular sieves to give approximately 1.9 g of 3-oxo-1,2-diazolidine para-toluenesulfonate salt: n.m.r. (90 MHz, DMSO-d$_6$): δ 8.8 (br. s, 3), 7.4 (d, 2, J=8), 7.0 (d, 2, J=8), 3.64 (t, 2, J=8), 2.5 (t, 2, J=8), 2.20 (s, 3); i.r. (KBr): 1750 cm$^{-1}$; m.s.: M$^+$=258.

Preparation 2

3-Oxo-1-(Methylene)-1,2-Pyrazolidinium Ylide Dimer

3-Oxo-1,2-diazolidine (25.8 g, 0.1 mmol) was was dissolved in methanol (200 ml). Aqueous formaldehyde (37%, 10.2 g, 0.125 mmol) was added to the solution followed by the addition of solid sodium bicarbonate (20 g) 1 minute later. The resultant mixture was stirred at room temperature for 45 minutes, filtered and the mother liquors were concentrated in vacuo. The solvent was azeotropically distilled in vacuo with isopropanol (3X, 500 ml) and the final residue was dried in vacuo. The resultant concentrate was refluxed in methylene chloride (600 ml) for 2 hours, filtered and concentrated in vacuo to give 6.4 g, 5% yield of a colorless solid of 3-oxo-1-(methylene)-1,2-pyrazolidinium ylide dimer: n.m.r. (90 MHz, CDCl$_3$): δ 4.7 (s, 4), 3.46 (t, 4, J=7), 2.56 (t, 4, J=7); i.r. (CHCl$_3$): 1700 cm$^{-1}$; m.s.: M$^+$=196.

Preparation 3

3-Oxo-1-(Dimethylmethylene)-1,2-Pyrazolidinium Ylide

3-Oxo-1,2-diazolidine p-toluenesulfonate salt (1.29 g, 5 mmol) was suspended in ethanol (10 ml). Acetone (0.5 ml) was added and the resultant solution was stirred for 1 minute. Solid sodium bicarbonate (1 g) was added and the resultant solution was stirred at room temperature for 45 minutes. The solution was filtered and the filter cake was washed with diethyl ether and concentrated in vacuo to give 570 mg of a colorless solid of 3-oxo-1-(dimethylmethylene)-1,2-pyrazolidinium ylide: n.m.r. (60 MHz, CDCl$_3$): δ 4.1 (t, 2, J=8), 2.6 (t, 2, J=8), 2.24 and 2.15 (2X s, 6); m.s.: M$^+$=126; m.p. 115°–125° C.

Preparation 4

3-Oxo-1-(Diphenylmethylene)-1,2-Pyrazolidinium Ylide

Benzophenone β-chloropropionyl hydrazyl (10.04 g, 35 mmol) was dissolved in THF (110 ml). Sodium hydride ((55% oily) 1.52 g, 35 mmol) was added to the solution in portions. The resultant mixture was stirred for 18 hours at room temperature, refluxed for 2 hours, cooled and washed with water. The organic phase was dried over magnesium sulfate, filtered and concentrated in vacuo. The solvent was azeotropically distilled in vacuo with toluene to leave approximately 5 g of a yellow solid of 3-oxo-1-(diphenylmethylene)-1,2-pyrazolidinium ylide: n.m.r. (60 MHz, CDCl$_3$): δ 8.1–7.1 (m, 10), 4.13 (t, 2, J=8), 3.64 (t, 2, J=8).

Preparation 5

3-Oxo-1-(Di(ethyl carboxylate)methylene)-1,2-Pyrazolidinium Ylide

3-Oxo-1,2-diazolidine p-toluenesulfonate salt (10 g, 38.75 mmol) was dissolved in DMF (100 ml). Diethylketomalonate (5.9 ml, 38.75 mmol) was added to the solution in the presence of molecular sieves (3 Å, 39 g). The reaction solution was stirred for 2 hours, solid sodium bicarbonate (7.75 g) was added and the resultant solution was stirred for 2.5 hours. Water (80 ml) and methylene chloride (80 ml) were added to the reaction solution. The molecular sieves were removed by filtration and washed with methylene chloride. The methylene chloride washed from the sieves was combined with the reaction solution, the layers were separated and the aqueous layer was washed with methylene chloride (1000 ml). The organic layer was dried over magnesium sulfate, filtered and the methylene chloride was removed in vacuo. The DMF was removed in vacuo in a short path (bulb to bulb) distillation and the product was dried in vacuo to give 3.6 g, 38.3% yield of 3-oxo-1-(di(ethyl carboxylate)methylene)-1,2-pyrazolidinium ylide: n.m.r. (90 MHz, CDCl$_3$): δ 4.92 (t, 2, J=8), 4.42 and 4.36 (2x q, 4, J=7), 2.84 (t, 2, J=8), 1.38 and 1.36 (2x t, 6, J=9,7); i.r. (CHCl$_3$): 1739, 1710 cm$^{-1}$; m.s.: M$^+$=242;

Anal. Calcd. for C$_{10}$H$_{14}$O$_5$N$_2$: Calcd.: C, 49.58; H, 5.83; N, 11.56; Found: C, 49.31; H, 5,62; N, 11.34. m.p.: 85°–89° C.

Preparation 6

3-Oxo-1-(2-(Trifluoromethyl)phenylmethylene)-1,2-Pyrazolidinium Ylide

3-Oxo-1,2-diazolidine p-toluenesulfonate salt (2.58 g, 10 mmol) dissolved in ethanol (absolute, 15 ml) was combined with 2-(trifluoromethyl)benzaldehyde (1.74 g, 10 mmol). The resultant mixture was stirred for 1 minute then solid sodium bicarbonate (2 g) was added. The mixture was stirred at room temperature for 45 minutes, filtered, and the filtrate was concentrated in vacuo. The residue was taken up in methylene chloride (200 ml), dried over magnesium sulfate, filtered, then concentrated in vacuo to give 2.22 g, 91% yield of 3-oxo-1-(2-(trifluoromethyl)phenylmethylene)-1,2-pyrazolidinium ylide: n.m.r. (CDCl$_3$, 90 MHz): δ 9.35 (br. d, 1, J=7), 7.3 (m, 4), 4.60 (t, 2, J=8), 2.8 (t, 2, J=8); m.s.: M$^+$=242; i.r. (CHCl$_3$): 1687 cm$^{-1}$.

Preparation 7

3-Oxo-1-(3-(Trifluoromethyl)phenylmethylene)-1,2-Pyrazolidinium Ylide

3-Oxo-1,2-diazolidine p-toluenesulfonate salt (2.58 g, 10 mmol) was dissolved in DMF (20 ml) and the solution was combined with 3-(trifluoromethyl)benzaldehyde (1.74 g, 10 mmol). The resultant solution was stirred for 1 minute, solid sodium bicarbonate (2 g) was added and the mixture was stirred for an additional 30 minutes at room temperature. The reaction solution was diluted with water (150 ml) then the resultant solution was extracted with methylene chloride. The organic extracts were concentrated in vacuo. The residue was dissolved in toluene (200 ml) then the solution was evaporated in vacuo to give a colorless solid. The solid was triturated with diethyl ether, collected by filtration and dried in vacuo overnight to give 2.08 g of 3-oxo-1-(3-(trifluoromethyl)phenylmethylene)-1,2-pyrazolidinium ylide: n.m.r. (CDCl$_3$, 90 MHz): δ 8.66 (d, 1, J=7), 8.32 (br, s, 1), 7.6 (m, 2), 7.16 (s, 1), 4.6 (t, 2, J=7) 2.8 (t, 2, J=7); m.s.: M$^+$=242; i.r. (CHCl$_3$): 1684, 1594 cm$^{-1}$; u.v.: (95% ethanol) λ$_{max}$=342 (ε=27,800), 329 (ε=28,400);

Anal. Calcd. for C$_{11}$H$_9$N$_2$OF$_3$: Theory: C, 54.55; H, 3.75; N, 11.57; F, 23.53. Found C, 54.77; H, 3.49; N, 11.72; F, 23.38.

m.p.: 166°–168° C.

EXAMPLE 1

2,3-Di(Allyl Carboxylate)-8-Oxo-1,5-Diazabicyclo[3.3.0]Octa-2-ene

3-Oxo-1-(methylene)-1,2-pyrazolidinium ylide dimer (196 mg, 1 mmol), diallyl butynediate (388 mg, 2 mmol) and acetonitrile (5 ml) were combined and refluxed for 3 hours. The reaction solution was cooled to room temperature and the small amount of precipitate that formed was removed by filtration. The filtrate was concentrated in vacuo to give 590 mg of yellow oil. The yellow oil was chromatographed on preparatory-scale thin layer chromatography plates, eluting with 1:1 hexane:ethyl acetate to give 270 mg, 46% yield of 2,3-di-(allyl carboxylate)-8-oxo-1,5-diazabicyclo[3.3.0]octa-2-ene: n.m.r. (90 MHz, CDCl$_3$): δ 6.1–5.7 (m, 2), 5.6–5.1 (m, 4), 4.84 (dm, 2, J=6), 4.64 (dm, 2, J=6,), 4.15 (s, 2), 3.20 (t, 2, J=7), 2.95 (t, 2, J=7); m.s.: M$^⊕$=292; u.v. (methanol): δ$_{max}$=340 (ε=3900); i.r. (CHCl$_3$): 1749, 1731, 1705 cm$^{-1}$.

EXAMPLE 2

2,3-Di(Sodium Carboxylate)-8-Oxo-1,5-Diazabicyclo[3.3.0]Octa-2-ene

Triphenylphosphine (18 mg, 0.07 mmol) and tetrakis[triphenylphosphine]palladium(O) (81 mg, 0.07 mmol) were slurried in acetone (5 ml). To the slurry was added on acetone solution (5 ml) of sodium 2-ethylhexanoate (745 mg, 4.5 mmol). The mixture was stirred for approximately 1 minute, an acetone solution (10 ml) of 2,3-di-(allyl carboxylate)-8-oxo-1,5-diazabicyclo[3.3.0]octa-2-ene (690 mg, 2.36 mmol) was added, and the reaction solution was stirred at room temperature for 2 hours. The resultant precipitate was collected by filtration under a blanket of nitrogen and dried in vacuo to give 580 mg of 2,3-di(sodium carboxylate)-8-oxo-1,5-diazabicyclo[3.3.0]octa-2-ene: n.m.r. (90 MHz, D$_2$O): δ 3.82 (s, 2, C-4 protons), 3.30 (t, 2, J=7), 2.80 (t, 2, J=7); u.v. (methanol): λ$_{max}$=335 (ε=3600); i.r. (KBr): 1671, 1646, 1635, 1624, 1594, 1580 cm$^{-1}$.

EXAMPLE 3

2,3-Di(Allyl Carboxylate)-4,4-Dimethyl-8-Oxo-1,5-Diazabicyclo[3.3.0]Octa-2-ene Diallyl butynedioate (800 mg, 4.1 mmol), methylene chloride (5 ml) and 3-oxo-1-(dimethylmethylene)-1,2-pyrazolidinium ylide (520 mg, 4.1 mmol) were combined and stirred at room temperature for 3 days. The reaction solution was concentrated in vacuo to a yellow oil and the oil was chromatographed on a preparatory scale (2 mm thick) thin layer chromatography plates eluted with 1:1 hexane:ethyl acetate. Three elutions yielded 600 mg, 45% yield of 2,3-di(allyl carboxylate)-4,4-dimethyl-8-oxo-1,5-diazabicyclo[3.3.0]octa-2-ene: n.m.r. (90 MHz, CDCl$_3$): δ 6.1–5.6 (m, 2), 5.4–5.1 (m, 4), 4.70 (dm, 2, J=6), 4.62 (dm, 2, J=6), 3.20 (t, 2, J=7), 2.76 (t, 2, J=7), 1.4 (s, 6); m.s.: M$^+$=320; u.v. (methanol): λ$_{max}$=355 (ε=8400), 220 (ε=9000); i.r. (CHCl$_3$): 1751, 1702 cm$^{-1}$;

Anal. Calcd. for C$_{16}$H$_{20}$N$_2$O$_5$: Theory: C, 59.99; H, 6.29; N, 8.74. Found: C, 59.96; H, 6.24; N, 8.62.

EXAMPLE 4

2,3-Di(Sodium Carboxylate)-4,4-Dimethyl-8-Oxo-1,5-Diazabicyclo[3.3.0]Octa-2-ene Triphenylphosphine (39 mg, 0.15 mmol) was dissolved in acetone (5 ml) and tetrakis[triphenylphosphine] palladium(O) (173 mg, 0.15 mmol) was added to the solution. An acetone solution (10 ml) of sodium 2-ethylhexanoate (1.66 g, 10 mmol) followed by an acetone solution (10 ml) of 2,3-di(allyl carboxylate)-4,4-dimethyl-8-oxo-1,5-diazabicyclo[3.3.0]octa-2-ene (1.6 g, 5 mmol) was added and the solution was stirred at room temperature for 2 hours. Then the resultant precipitate was collected by filtration and dried first in vacuo at room temperature then at 40° C. in vacuo for 3 hours. The precipitate was dissolved in distilled water (100 ml), washed with methylene chloride and ether and lyophilized to give 1.25 g of 2,3-di(sodium carboxylate)-4,4-dimethyl-8-oxo-1,5-diazabicyclo[3.3.0]octa-2-ene: n.m.r. (90 MHz, D$_2$O): δ 3.50 (t, 2, J=7), 3.10 (t, 2, J=7), 1.56 (s, 6); u.v. (water): λ$_{max}$=310 (ε=4100); i.r. (KBr): 1684, 1629, 1610, 1576 cm$^{-1}$.

EXAMPLE 5

2,3-Di(Allyl Carboxylate)-4,4-Diphenyl-8-Oxo-1,5-Diazabicyclo[3.3.0]Octa-2-ene Diallyl butynedioate (776 mg, 4 mmol), 3-oxo-1-(diphenylmethylene)-1,2-pyrazolidinium ylide (1.0 g, 4 mmol) and methylene chloride (5 ml) were combined and stirred at room temperature for 4 days then concentrated in vacuo. The concentrate was triturated with absolute ethanol (3X, 5 ml) at 0° C., dried in vacuo to give 1.33 g, 75% yield of 2,3-di(allyl carboxylate)-4,4-diphenyl-8-oxo-1,5-diazabicyclo[3.3.0]octa-2-ene: n.m.r. (90 MHz, CDCl$_3$): δ 7.38 (m, 10, aromatic protons), 6.2–4.9 (m, 6, unsaturated protons of allyl groups), 4.84 (m, 2, C-1 protons of allyl group on C-2 carboxylate group), 4.45 (m, 2, C-1 protons on allyl group of C-3 carboxylate group), 2.66 (m, 4, C-6 and C-7 protons); m.s.: M$^+$=444; u.v. (methanol): $\lambda_{max}$=350 (ε=5450), 237 (ε=10,100); i.r. (CHCl$_3$): 1749, 1710 cm$^{-1}$;

Anal. Calcd. for C$_{26}$H$_{24}$N$_2$O$_5$: Theory: C, 70.26; H, 5.44; N, 6.30. Found: C, 70.50; H, 5.49; N, 6.40.

EXAMPLE 6

2,3-Di(Sodium Carboxylate)-4,4-Diphenyl-1,5-Diazabicyclo[3.3.0]Octa-2-ene

Tetrakistriphenylphosphine]palladium(O) (58 mg, 0.05 mmol) was slurried in acetone (5 ml) then triphenylphosphine (13 mg, 0.05 mmol) followed by sodium 2-ethylhexanaoate (730 mg, 4.4 mmol) were added. To this slurry was added a solution of 2,3-di(allyl carboxylate)-4,4-diphenyl-8-oxo-1,5-diazabicyclo[3.3.0]-octa-2-ene (888 mg, 2 mmol) in acetone (10 ml). The reaction mixture was stirred at room temperature for three hours. The precipitate which resulted was collected by filtration, dried in vacuo overnight, then triturated with acetone and dried in vacuo to give 2,3-di(sodium carboxylate)-4,4-diphenyl-1,5-diazabicyclo[3.3.0]octa-2-ene: n.m.r. (90 MHz, D$_2$O): δ 7.40 (s, 10, aromatic protons), 3.0–2.6 (m, 4, C-6 and C-7 protons); u.v. (water): $\lambda_{max}$=315 (ε=5500); i.r. (KBr): 1680, 1605, 1577 cm$^{-1}$.

EXAMPLE 7

2,3-Di(Allyl Carboxylate)-4,4-Di(Ethyl Carboxylate)-8-Oxo-1,5-Diazabicyclo[3.3.0]Octa-2-ene Diallyl butynedioate (388 mg, 2 mmol) and 3-oxo-1-(diethyl carboxylate)methylene)-1,2-pyrazolidinium ylide (484 mg, 2 mmol) were dissolved in methylene chloride (5 ml) and stirred for 48 hours at room temperature. The reaction mixture was concentrated in vacuo to give a yellow oil which was chromatographed on preparatory-scale thin layer chromatography plates eluted with 1:1 hexane:ethyl acetate. The chromatography yielded 610 mg, 70% yield of 2,3-di(allyl carboxylate)-4,4-di(ethyl carboxylate)-8-oxo-1,5-diazabicyclo[3.3.0]octa-2-ene: n.m.r. (90 MHz, CDCl$_3$): δ 6.1–5.6 (m, 2), 5.5–5.1 (m, 4), 4.76 (dm, 2, J=6), 4.60 (dm, 2, J=6), 4.24 (q, 4, J=8), 3.52 (t, 2, J=7), 2.88 (t, 2, J=7), 1.25 (t, 6, J=8); m.s.: M$^+$=363 (M-CO$_2$Et); u.v. (methanol): $\lambda_{max}$=350 (ε=6900), 260 (shoulder, ε=3000), 215 (ε=8400); i.r. (CHCl$_3$): 1742, 1716 cm$^{-1}$;

Anal. Calcd. for C$_{20}$H$_{24}$N$_2$O$_9$: Theory: C, 55.04; H, 5.54; N, 6.42. Found: C, 54.88; H, 5.35; N, 6.27.

EXAMPLE 8

2,3-Di(Sodium Carboxylate)-4,4-Di(Ethyl Carboxylate)-8-Oxo-1,5-Diazabicyclo[3.3.0]Octa-2-ene Monohydrate Triphenylphosphine (52 mg, 0.2 mmol) was dissolved in acetone (5 ml) then tetrakis[triphenylphosphine]palladium(O) (234 mg, 0.2 mmol) was added. After approximately 5 minutes sodium 2-ethylhexanoate (2.24 g, 13.52 mmol) was added along with additional acetone (10 ml). Once all the components were in solution, an acetone solution (15 ml) of 2,3-di(allyl carboxylate)-4,4-di(ethyl carboxylate)-8-oxo-1,5-diazabicyclo[3.3.0]octa-2-ene (2.95 g, 6.76 mmol) was added and the mixture was stirred at room temperature for 2 hours. The precipitate which formed was collected by filtration and dried in vacuo to give 2.7 g of 2,3-di(sodium carboxylate)-4,4-di(ethyl carboxylate)-8-oxo-1,5-diazabicyclo[3.3.0]octa-2-ene monohydrate: n.m.r. (90 MHz, D$_2$O): δ 4.30 (q, 4, J=7), 3.50 (t, 2, J=8), 3.0 (t, 2, J=8), 1.30 (t, 6, J=7); u.v. (water): $\lambda_{max}$=310 (ε=6600), 255 (shoulder, ε=4000); i.r. (KBr): 1745, 1706, 1681, 1640, 1624, 1590 cm$^{-1}$.

EXAMPLE 9

2-Phenyl-3-(Allyl Carboxylate)-8-Oxo-1,5-Diazabicyclo[3.3.0]Octa-2-ene

Under a nitrogen atmosphere, allyl 3-phenylprop-2-ynoate (1.90 g, 10.2 mmol), acetonitrile (12 ml), and 3-oxo-1-methylene-1,2-pyrazolidinium ylide dimer (1.00 g, 5.1 mmol) were combined and the solution was refluxed for 6 hours. The solution was filtered, concentrated in vacuo, and chromatographed on silica gel eluted with a solvent gradient of 0–70% ethyl acetate in hexane. The chromatography yielded 0.365 g of 2-phenyl-3-(allyl carboxylate)-8-oxo-1,5-diazabicyclo[3.3.0]-octa-2-ene: n.m.r. (90 MHz, CDCl$_3$): δ 7.60–7.25 (m, 5, aromatic protons), 5.96–5.55 (m, 1, methine proton of allyl group), 5.16 (m, 1, sp$^2$ methylene proton of allyl group), 5.00 (m, 1, sp$^2$ methylene proton of allyl group), 4.53 (dt, 2, sp$^3$ methylene protons of allyl group), 4.16 (s, 2, C-4 protons), 3.34 (t, 2, C-7 protons), 2.85 (t, 2, C-6 protons); i.r. (CHCl$_3$) 1726, 1691, 1358, 1336, 1290, 1241, 1229, 1215, 1194, and 1112 cm$^{-1}$; u.v. (methanol): $\lambda_{max}$=349 (ε=13,000), 243 (ε=9800, shoulder); m.s.: M$^+$=284 (0.68), (M-1)$^+$=283 (0.69);

Anal. Calcd. for C$_{16}$H$_{16}$O$_3$N$_2$: Theory: C, 67.59; H, 5.67; N, 9.85. Found: C, 67.86; H, 5.69; N, 9.58.

EXAMPLE 10

2-Phenyl-3-(Sodium Carboxylate)-8-Oxo-1,5-Diazabicyclo[3.3.0]Octa-2-ene

Under a nitrogen atmosphere, palladium(II) acetate (0.007 g, 0.031 mmol) was dissolved in dry acetone (5 ml). Triphenylphosphine (0.066 g, 0.25 mmol) was added and the solution was stirred until a precipitate formed. Sodium 2-ethylhexanoate (0.174 g, 1.05 mmol) was added to this suspension and the mixture was stirred until solution was affected. An acetone solution (8 ml) of 2-phenyl-3-(allyl carboxylate)-8-oxo-1,5-diazabicyclo[3.3.0]octa-2-ene (0.300 g, 1.05 mmol) was added and the reaction solution was stirred for 3 hours at room temperature. The solution was centrifuged with diethyl ether (10 ml). After centrifugation, the supernatant solvent was decanted and the remaining precipitate was dried in vacuo to give 2-phenyl-3-(sodium carboxylate)-8-oxo-1,5-diazabicyclo[3.3.0]octa-2-ene: n.m.r. (90 MHz, D$_2$O): δ 7.36 (s, 5, aromatic protons), 4.03 (s, 2, C-4 protons), 3.42 (t, 2, C-7 protons), 2.90 (t, 2, C-6 protons).

EXAMPLE 11

2-Phenyl-3-(Allyl Carboxylate)-4,4-Dimethyl-8-Oxo-1,5-Diazabicyclo[3.3.0]Octa-2-ene Under nitrogen atmosphere, 3-oxo-1-(dimethylmethylene)-1,2-pyrazolidinium ylide (2.52 g, 20.0 mmol), allyl 3-phenylprop-2-ynoate (3.72 g, 20.0 mmol) and dry methylene chloride (25 ml) were combined. The reaction solution was stirred at room temperature for one week, filtered and concentrated under reduced pressure. The concentrate and acetonitrile (25 ml) were combined and refluxed under nitrogen overnight and chromatographed on silica gel eluted with a gradient of 0 to 50% ethyl acetate in hexane. Combination of the product-containing fractions yielded 0.38 g, 6.1% yield of the 2-phenyl-3-(allyl carboxylate)-4,4-dimethyl-8-oxo-1,5-diazabicyclo[3.3.30]octa-2-ene: n.m.r. (90 MHz, CDCl$_3$): δ 7.36 (m, 5, aromatic protons), 5.88–5.44 (m, 1, methine proton of allyl group), 5.12–4.80 (m, 2, sp$^2$ methylene protons of the allyl group), 4.44 (dt, 2, sp$^3$ protons of allyl group), 3.26 (t, 2, C-7 protons), 2.96 (t, 2, C-6 protons), 1.45 (s, 6, protons of 4,4-dimethyl groups); i.r. (CHCl$_3$) 1720, 1689, 1403, 1382, 1362, 1342, 1233, 1215, 1204, 1165 cm$^{-1}$; u.v. (methanol) λ$_{max}$=347 (ε=7600), 238 (ε=7200); m.s.: M$^+$=312;

Anal. Calcd. for C$_{18}$H$_{20}$O$_3$N$_2$: Theory: C, 69.21; H, 6.45; N, 8.97. Found: C, 69.10; H, 6.28; N, 8.74.

EXAMPLE 12

2-Phenyl-3-(Sodium Carboxylate)-4,4-Dimethyl-8-Oxo-1,5-Diazabicyclo[3.3.0]Octa-2-ene Palladium(II) acetate (0.0043 g, 0.019 mmol) and ethyl acetate were combined under a nitrogen atmosphere. Triphenylphosphine (0.042 g, 0.160 mmol) and ethyl acetate (1 ml) were added to the stirred solution. After an additional 10 minutes of stirring, a precipitate formed and sodium 2-ethylhexanoate (0.106 g, 0.64 mmol) was added. After solution was affected, 2-phenyl-3-(allyl carboxylate)-4,4-dimethyl-8-oxo-1,5-diazabicyclo[3.3.0]octa-2-ene (0.200 g, 0.64 mmol) in ethyl acetate (5 ml) was added and the solution was stirred under nitrogen at room temperature for 2 hours. The resultant precipitate was collected by suction filtration and dried in vacuo to yield 0.130 g, 70% yield of a pale tan solid of 2-phenyl-3-(sodium carboxylate)-4,4-dimethyl-8-oxo-1,5-diazabicyclo[3.3.0]octa-2-ene: n.m.r. (90 MHz, D$_2$O): δ 7.34 (s, 5, aromatic protons), 3.37 (t, 2, C-7 protons), 2.96 (t, 2, C-6 protons), 1.40 (s, 6, protons of 4,4-dimethyl groups); i.r. (KBr): 1673, 1577, 1558, 1377, 1362 cm$^{-1}$; u.v. (methanol): λ$_{max}$=244 (ε=8400), 310 (ε=6500).

EXAMPLE 13

3-(Allyl Carboxylate)-4,4-Dimethyl-8-Oxo-1,5-Diazabicyclo3.3.0]Octa-2-ene

3-Oxo-1-(dimethylmethylene)-1,2-pyrazolidinium ylide (3.98 g, 30 mmol), allyl prop-2-ynoate (3.3 g, 30 mmol) and methylene chloride (30 ml) were combined under nitrogen and stirred at room temperature for 4 days. The reaction solution was concentrated to an oil in vauco and chromatographed by preparatory-scale HPLC on silica gel eluted with 1:1 hexane:ethyl acetate. The chromatography yielded 4.77 g, 67% yield of 3-(allyl carboxylate)-4,4-dimethyl-8-oxo-1,5-diazabicyclo[3.3.0]octa-2-ene: n.m.r. (90 MHz, CDCl$_3$): δ 7.3 (s, 1, C-2 proton), 6.16–5.6 (m, 1, methine proton of allyl group), 5.4–5.1 (m, 2, sp$^2$ methylene protons of allyl group), 4.62 (dm, 2, J=5, sp$^3$ protons of allyl group), 3.24 (t, 2, J=7, C-7 protons), 2.84 (t, 2, J=7, C-6 protons), 1.44 (s, 6, protons of 4,4-dimethyl groups); i.r. (CHCl$_3$) 1693, 1593 cm$^{-1}$; u.v. (methanol): λ$_{max}$=348 (ε=9900); m.s.: M$^+$=236.

EXAMPLE 14

3-(Sodium Carboxylate)-4,4-Dimethyl-8-Oxo-1,5-Diazabicyclo[3.3.0]Octa-2-ene

Under a nitrogen atmosphere, palladium(II) acetate (0.034 g, 0.15 mmol) and dry acetone (25 ml) were combined. Triphenylphosphine (0.197 g, 0.75 mmol) was added and the reaction solution was stirred under nitrogen until a precipitate formed. Sodium 2-ethylhexanoate (0.831 g, 5.0 mmol) was added and the reaction mixture was stirred until a solution was affected. 3-(Allyl carboxylate)-4,4-dimethyl-8-oxo-1,5-diazabicyclo[3.3.0]octa-2-ene (1.18 g, 5.0 mmol) was added as an acetone solution (15 ml) and the reaction was stirred at room temperature for 2 hours. The solid that formed was collected by suction filtration, rinsed with acetone and dried in vacuo overnight at room temperature to yield 0.98 g, 90% yield of 3-(sodium carboxylate)-4,4-dimethyl-8-oxo-1,5-diazabicyclo[3.3.0]octa-2-ene: n.m.r. (90 MHz, D$_2$O): δ 6.95 (s, 1, C-2 proton), 3.30 (t, 2, C-7 protons), 2.85 (t, 2, C-6 protons), 1.32 (s, 6, methylene protons of the 4,4-dimethyl groups); i.r. (KBr): 1672, 1609, 1555, and 1361 cm$^{-1}$; u.v. (methanol); λ$_{max}$=319 (ε=8200), 209 (ε=8200).

EXAMPLE 15

2-(Allyl Carboxylate)-3-(Methyl Carboxylate)-8-Oxo-1,5-Diazabicyclo[3.3.0]Octa-2-ene and the Corresponding 2,3-Regioisomer 3-Oxo-1-methylene-1,2-pyrazolidinium ylide dimer (365 mg, 1.86 mmol) and allyl methyl butynidioate (625 mg, 3.72 mmol) were combined in acetonitrile (10 ml). The mixture was stirred and refluxed under nitrogen for 1.5 hour, allowed to cool to room temperature then concentrated in vacuo. The residue was chromatographed on silica gel eluted with a solvent gradient of 0 to 50% ethyl acetate in hexane. The product-containing fractions were combined to give 0.21 g, 30% yield of 2-(allyl carboxylate)-3-(methyl carboxylate)-8-oxo-1,5-diazabicyclo[3.3.0]octa-2-ene and the corresponding 2,3-regioisomer: n.m.r. (90 MHz, CDCl$_3$): δ 6.17–5.63 (m, 2), 5.48–5.12 (m, 4), 4.83+4.62 (2x d, 2), 4.10 (s, 4), 3.90+3.72 (2x s, 3), 3.35 (t, 4), 2.82 (t, 4); m.s.: M$^+$=266; u.v. (methanol): λ$_{max}$=212 (ε=7,000, shoulder), 344 (ε=5100).

EXAMPLE 16

2-(Methyl Carboxylate)-3-(Sodium Carboxylate)-8-Oxo-1,5-Diazabicyclo[3.3.0]Octa-2-ene and the Corresponding 2,3-Regioisomer Under a nitrogen atmosphere, palladium(II) acetate (0.008 g, 0.35 mmol) and ethyl acetate (3 ml) were combined. To the slurry was added triphenylphosphine (0.071 g, 0.27 mmol) and ethyl acetate (approximately 2 ml). Upon formation of a precipitate, sodium 2-ethylhexanoate (0.188 g, 1.13 mmol) was rinsed into the solution with an additional amount of ethyl acetate (approximately 3 ml). The solution was stirred under nitrogen at room temperature for an additional 10 minutes. A mixture of 2-(methyl carboxylate)-3-(allyl carboxylate)-8-oxo-1,5-diazabicyclo[3.3.0]octa-2-ene and the corresponding 2,3-regioisomer (0.300 g, 1.13 mmol) was added as a solution in ethyl acetate (4 ml) and rinsed in with an additional amount of ethyl acetate (approximately 3 ml). The solution was stirred for 2.5 hours at room temperature, filtered and the collected precipitate dried in vacuo at 30° C. to yield 0.256 g, 91% yield of a pale yellow solid of the 2-(methyl carboxylate)-3-(sodium carboxylate)-8-oxo-1,5-diazabicyclo[3.3.0]octa-2-ene and the corresponding 2,3regioisomer: n.m.r. (270 MHz, $D_2O$): δ 4.84 (s, 6), 4.52–4.32 (m, 1), 4.23–3.65 (m, 7), 3.65–3.35 (m, 2), 3.05–2.85 (m, 1), 2.85–2.70 (m, 1); i.r. (KBr): 1723, 1718, 1691, 1600, 1406, 1369, 1346, 1323, 1279 $cm^{-1}$; u.v. (methanol): $\lambda_{max}$=220 (ε=6600, shoulder), 325 (ε=3700).

EXAMPLE 17

2,3-Di(Allyl Carboxylate)-4-(R,S)-(2-Trifluoromethylphenyl)-8-Oxo-1,5-Diazabicyclo[3.3.0]-Octa-2-ene Diallyl butynedioate (1.603 g, 8.26 mmol) and -oxo-1-(2-(trifluoromethyl)phenylmethylene)-1,2-pyrazolidinium ylide (2.0 g, 8.26 mmol) and methylene chloride (10 ml) were combined and stirred at room temperature for 36 h. The reaction solution was concentrated in vacuo to give 3.6 g of a yellow gum. The gum was chromatographed by preparatory-scale HPLC on silica gel eluted with a gradient of 0 to 25% ethyl acetate in hexane to give 3.18 g, 88% yield of the 2,3-di(allyl carboxylate)-4-(R,S)-(2-(trifluoromethyl)phenyl-8-oxo-1,5-diazabicyclo[3.3.0]octa-2-ene: n.m.r. (90 MHz, $CDCl_3$): δ 7.5 (m, 4), 6.2–5.8 (m, 2), 5.75 (br. s, 1), 5.6–5.0 (m, 4), 4.88 (dm, 2, J=6), 4.45 (dm, 2, J=6), 3.5–2.7 (m, 4): m.s.: $M^+$=436; i.r. ($CHCl_3$): 1750, 1730, 1709 $cm^{-1}$; u.v. (95% ethanol): $\lambda_{max}$=343 (ε=6520).

EXAMPLE 18

2,3-Di(Sodium Carboxylate)-4-(R,S)-(2-(Trifluoromethyl)phenyl)-8-Oxo-1,5-Diazabicyclo[3.3.0]-Octa-2-ene Tetrakis[triphenylphosphine]palladium(O) (231 mg, 0.2 mmol) was slurried in ethyl acetate (10 ml). Triphenylphosphine (53 mg, 0.2 mmol), and sodium 2-ethylhexanoate (2.12 g, 12.8 mmol), and a solution of 2,3-di(allyl carboxylate)-4-(2-(trifluoromethyl)phenyl)-8-oxo-1,5-diazabicyclo[3.3.0]octa-2-ene (2.8 g, 6.4 mmol) in ethyl acetate (35 ml) were added sequentially to the slurry and the resultant solution was stirred at room temperature for 4 h. The precipitate formed was collected by filtration, dried in vacuo overnight, taken up in water (200 ml), and washed with ethyl acetate, methylene chloride and diethyl ether. The aqueous phase was lyophilized to give 2.1 g, 82% of crude title product. The crude product was triturated several times with ethyl acetate and dried in vacuo to give 2,3-di(sodium carboxylate)-4-(R,S)-(2-(trifluoromethyl)-phenyl)-8-oxo-1,5-diazabicyclo[3.3.0]octa-2-ene: n.m.r. ($D_2O$, 90 MHz): δ 7.8–7.3 (m, 4), 5.56 (s, 1), 3.26 (t, 2, J=8), 2.72 (t, 2, J=8); i.r. (KBr): 1663, 1621, 1592 $cm^{-1}$; u.v. (95% ethanol): $\lambda_{max}$=340 (ε=2300);

Anal. Calcd. for: $C_{15}H_9N_2O_5Na_2$: Theory: C, 45.02; H, 2.27; N, 7.00; F, 14.24. Found: C, 44.97; H, 2.37; N, 6.85; F, 14.45.

EXAMPLE 19

2,3-Di(Allyl Carboxylate)-4-(R,S)-(3-(Trifluoromethyl)phenyl)-8-Oxo-1,5-Diazabicyclo[3.3.0]Octa-2-ene 3-oxo-1-(3-(trifluoromethyl)phenylmethylene)-1,2-pyrazolidinium ylide (1.95 g, 8 mmol), diallyl butynedioate (1.56 g, 8 mmol) and 1,2-dichloroethane (20 ml) were combined and stirred at room temperature overnight. The reaction solution was concentrated in vacuo and chromatographed by preparatory-scale HPLC on silica gel eluted with a gradient of 0 to 25% ethyl acetate in hexane. The chromatography yielded 2.62 g, 75% yield of 2,3-di(allyl carboxylate)-4-(R,S)-(3-(trifluoromethyl)phenyl)-8-oxo-1,5-diazabicyclo[3.3.0]-octa-2-ene: n.m.r. ($CDCl_3$, 90 MHz): δ 7.9–7.3 (m, 4), 6.2–5.9 (m, 7), 5.8 (d, 2, J=6), 5.5 (d, 2, J=6), 4.2 (t, 2, J=6), 2.96 (t, 2, J=6); i.r. ($CHCl_3$) 1725 $cm^{-1}$; m.s.: M+1=435.

EXAMPLE 20

2,3-Di(Sodium Carboxylate)-4-(R,S)-(3-(trifluoromethyl)phenyl)-8-Oxo-1,5-Diazabicyclo[3.3.0]Octa-2-ene Tetrakis[triphenylphosphine]palladium(O) (183 mg, 0.158 mmol) was slurried in ethyl acetate (10 ml). Triphenylphosphine (41 mg, 0.158 mmol), sodium 2-ethylhexanoate (1.75 g, 10.55 mmol) and ethyl acetate (10 ml) were added to the slurry. A solution of 2,3-Di(allyl carboxylate)-4-(R,S)-(3-(trifluoromethyl)-phenyl)-8-oxo-1,5-diazabicyclo[3.3.0oxa-2-ene (2.30 g, 5.27 mmol) in ethyl acetate (20 ml) was added and the reaction solution was stirred at room temperature for 4 hours. The precipitate that formed was collected by filtration and dried in vacuo to give approximately 1.2 g of solid. The solid was taken up in water and washed with ethyl acetate and diethylether. The aqueous phase was stirred with charcoal, filtered through celite and the filtrate was lyophilized to yield 1.2 g of 2,3-di(sodium carboxylate)-4-(R,S)-(3-(trifluoromethyl)-phenyl)-8-oxo-1,5-diazabicyclo[3.3.0]octa-2-ene: n.m.r. ($D_2O$, 90 MHz): δ 7.6 (m, 4), 4.1 (t, 2, J=7), 3.54 (s, 1), 2.5 (t, 2, J=7); i.r. (KBr) 1584 $cm^1$.

EXAMPLE 21

2-(Benzyl Carboxylate)-3-Trifluoromethyl-8-Oxo-1,5-Diazabicyclo[3.3.0]Octa-2-ene 3-Oxo-1-(methylene)-1,2-pyrazolidinium ylide dimer (300 mg, 1.5 mmol) was added to a refluxing acetonitrile solution (5 ml) of benzyl 4,4,4-trifluoro-2-butynoate (456 mg, 2 mmol). The reaction solution was refluxed for 3 hours allowed to cool then concentrated in vacuo. The residue was chromatographed on preparatory-scale thin layer chromatography plates eluted with a 2:1 hexane:ethyl acetate mixture to yield 40 mg of 2-(benzyl carboxylate)-3-trifluoromethyl-8-oxo-1,5-diazabicyclo[3.3.0]octa-2-ene: n.m.r. ($CDCl_3$, 90 MHz): δ 7.36 (s, 5), 5.32 (s, 2), 4.06 (q, 2, J=2), 3.34 (t, 2), 2.82 (t, 2, J=8).

We claim:

1. A compound of the formula:

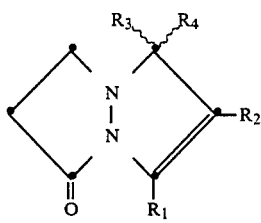

wherein
either $R_1$ and $R_2$ is hydrogen, $C_1$ to $C_6$ alkyl, substituted $C_1$ to $C_6$ alkyl substituted with one or two halogen, hydroxy, protected hydroxy, amino, protected amino, $C_1$ to $C_7$ acyloxy, nitro, carboxy, protected carboxy, carbaoyl, carbamoyloxy, cyano, methylsulfonylanimo or $C_1$ to $C_4$ alkyl, $C_7$ to $C_{12}$ phenylalkyl, $C_7$ to $C_{12}$ phenylalkyl wherein the $C_1$ to $C_6$ alkyl portion is substituted $C_1$–$C_6$ alkyl as defined above and wherein; the phenyl group may also be substituted phenyl substituted by 1 or 2 groups chosen from the group consisting of halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl, and a methylsulfornylamino group; phenyl, substituted phenyl as defined above; nitro or cyano; a group of the formula

—$CX_3$ wherein X is fluoro, chloro, bromo or iodo;
a group of the formula

wherein Z is 0, 1, 2 and $R_5$ is $C_1$ to $C_6$ alkyl, substituted $C_1$ to $C_6$ alkyl as defined above; phenyl, substituted phenyl as defined above; $C_7$ to $C_{12}$ phenylalkyl, $C_7$ to $C_{12}$ phenylalkyl substituted on the $C_1$ to $C_6$ alkyl portion as defined above, and wherein the phenyl portion is substituted phenyl as defined above;
a group of the formula

—$COR_6$ wherein $R_6$ is hydrogen, $C_1$ to $C_6$ alkyl, substituted $C_1$ to $C_6$ alkyl as defined above; perfluoro $C_2$ to $C_4$ alkyl, trihalomethyl, $C_7$ to $C_{12}$ phenylalkyl, $C_7$ to $C_{12}$ phenylalkyl substituted on the $C_1$ to $C_6$ alkyl portion or the phenyl portion as defined above; phenyl or substituted phenyl as defined above; a group of the formula

—$COOR_7$ wherein $R_7$ is hydrogen, an organic or inorganic cation chosen from the group consisting of lithium, sodium, potassium, barium and calcium cations, ammonium, dibenzylammonium, benzylammonium, 2-hydroxyethylammonium, bis(2-hydroxyethyl)ammonium, phenylethylbenzylammonium, dibenzylethylenediammonium, the protonated forms of procaine, quinine, N-methylglucosamine, glycine, ornithine, histidine, phenylglycine, lysine and arginine; $C_1$ to $C_6$ alkyl, substituted on the $C_1$ to $C_6$ alkyl as defined above; $C_7$ to $C_{12}$ phenylalkyl, $C_7$ to $C_{12}$ phenylalkyl substituted on the $C_1$ to $C_6$ alkyl portion or phenyl portion as defined above phenyl, substituted phenyl as defined above; a carboxy protecting group, or a non-toxic, metabolically-labile ester-forming group chosen from the group consisting of methoxymethyl, ethoxymethyl, iso-propoxymethyl, methoxyethyl, ethoxyethyl, propoxyethyl, iso-propoxyethyl, 5-methyl-2-oxo-1,3-dioxolen-4-ylmethyl, 5-phenyl-2-oxo-1,3-dioxolen-4-ylmethyl, methylthiomethyl, ethylthiomethyl, iso-propylthiomethyl, pivloyloxymethyl, α-acetoxymethyl, ethoxycarbonyl-1-methyl, α-acetoxyethyl, 3-phthalidyl, 5,6-dimethylphthalidyl, 1-(ethoxycarbonyloxy)-eth-1-yl, and 1-(methylaminocarbonyloxy)eth-1-yl; and the other of $R_1$ or $R_2$ is a group of the formula

—$COOR_9$ wherein $R_9$ is hydrogen, an organic or inorganic cation chosen from the group consisting of lithium, sodium, potassium, barium and calcium cations, ammonium, dibenzylammonium, benzylammonium, 2-hydroxyethylammonium, bis(2-hydroxyethyl)ammonium, phenylethylbenzyl ammonium, dibenzylethylenediammonium, the protonated forms of procaine, quinine, N-methylglucosamine, glycine, ornithine, histidine, phenylglycine, lysine and arginine a carboxy protecting group, or a non-toxic, metabolically-labile ester-forming group as defined above for $R_7$; and $R_3$ and $R_4$ are the same or different and are hydrogen, $C_1$ to $C_6$ alkyl, substituted $C_1$ to $C_6$ alkyl as defined above for $R_1$ or $R_2$ $C_7$ to $C_{12}$ phenylalkyl, $C_7$ to $C_{12}$ phenylalkyl substituted on the $C_1$ to $C_6$ alkyl portion or the phenyl portion as defined above for $R_1$ or $R_1$; phenyl, substituted phenyl as defined above for $R_1$ or $R_2$; or a group of the formula

—$COOR_{10}$ wherein $R_{10}$ has the same definition as $R_7$;
with the exception that, when $R_1$ and $R_2$ are a group of the formula

—$COOCH_3$, $R_3$ and $R_4$ are not methyl; or a pharmaceutically-acceptable salt thereof.

2. A compound of claim 1, wherein either $R_1$ and $R_2$ is
(A) a group of the formula —$CX_3$;
(B) a group of the formula

(C) a group of the formula

—$COR_6$;

and the other of $R_1$ or $R_2$ is a group of the formula

—COOR$_9$; and

R$_3$ and R$_4$ are the same or different and are hydrogen, C$_1$ to C$_6$ alkyl, phenyl, phenyl substituted with one or two moieties chosen from the group consisting of halogen, hydroxy, protected hydroxy, cyano nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminoethyl, protected aminomethyl, trifluoromethyl and methylsulfonylamino; or a group of the formula

COOR$_{10}$.

3. A compound of claim 1, wherein either R$_1$ and R$_2$ is
(A) hydrogen;
(B) phenyl;
(C) a group of the formula —CX$_3$; or (D) a group of the formula

—COOR$_7$;

and the other of R$_1$ and R$_2$ is a group of the formula

—COOR$_9$;

and R$_3$ and R$_4$ are:
(A) the same and are hydrogen, C$_1$ to C$_6$ alkyl, phenyl or a group of the formula —COOR$_{10}$; or (B) different, and either is hydrogen and the other is phenyl substituted with one or two moieties chosen from the group consisting of halogen, hydroxy, protected hydroxy, cyano, nitro, C$_1$ to C$_6$ alkyl, C$_1$ to C$_4$ alkoxy, carboxy, protected carboxy, carboxymethyl, protected carboxymethyl, hydroxymethyl, protected hydorxymethyl, aminomethyl, protected aminomethyl, trifluoromethyl and methylsulfonylamino.

4. A compound of claim 2, wherein either R$_1$ or R$_2$ is a group of the formula

—COOR$_7$ wherein both R$_7$ and R$_9$ are sodium, hydrogen or allyl.

5. A compound of claim 3, wherein R$_3$ and R$_4$ are the same and are a group of the formula

—COOR$_{10}$ wherein R$_{10}$ is ethyl.

6. A compound of claim 2, wherein R$_3$ and R$_4$ are phenyl.

7. A compound of claim 3, wherein R$_3$ and R$_4$ are the same and are methyl.

8. A compound of claim 3, wherein R$_3$ and R$_4$ are the same and are hydrogen.

9. A compound of claim 3, wherein either R$_3$ or R$_4$ is hydrogen and the other of R$_3$ or R$_4$ is 2-trifluoromethyl)phenyl.

10. A compound of claim 3, wherein either R$_3$ or R$_4$ is hydrogen and the other of R$_3$ or R$_4$ is 3-(trifluoromethyl)phenyl.

11. A compound of claim 2, wherein R$_1$ is a group of the formula

—COOR$_9$ wherein
R$_9$ is hydrogen, sodium or allyl;
R$_2$ is a group of the formula —COOCH$_3$;
and R$_3$ and R$_4$ are the same and are hydrogen.

12. A compound of claim 2, wherein R$_1$ is a group of the formula

—COOR$_9$ wherein R$_9$ is benzyl, allyl, sodium or hydrogen, R$_2$ is a group of the formula

—CX$_3$ wherein
X is fluoro;
and R$_3$ and R$_4$ are each hydrogen.

13. A compound of claim 2, wherein R$_1$ is hydrogen, phenyl or a group of the formula —COOCH$_3$; and R$_2$ s a group of the formula

—COOR$_9$ wherein R$_9$ is hydrogen, sodium or allyl.

14. A compound of claim 13, wherein, R$_1$ is phenyl and R$_3$ and R$_4$ are each hydorgen.

15. A compound of claim 13, wherein R$_1$ is phenyl and R$_3$ and R$_4$ are each methyl.

16. A compound of claim 13, wherein R$_1$ is hydrogen and R$_3$ and R$_4$ are each methyl.

17. A compound of claim 13, wherein R$_1$ is a group of the formula

—COOCH$_3$ and R$_3$ and R$_4$ are each hydrogen.

18. A pharmaceutical composition useful for the control of gram-positive and gram-negative bacterial infections, comprising a suitable vehicle and a therapeutically effective amount of the compound of claim 1, wherein R$_9$ is other then a carboxy protecting group and, wherein any amino, hydroxy and carboxy groups present in R$_1$, R$_2$, R$_3$ R$_4$ are unprotected.

19. A method for the treatment of gram-positive and gram-negative bacterial infections, which comprises administering to the infected host a therapeutically effective amount of the compound of claim 1 wherein R$_9$ is other than a carboxy protecting group and, wherein any amino, hydroxy and carboxy groups present in R$_1$, R$_2$, R$_3$, and R$_4$ are unprotected.

* * * * *